(12) United States Patent
Howe

(10) Patent No.: US 7,747,065 B2
(45) Date of Patent: Jun. 29, 2010

(54) PIXEL POSITIONING SYSTEMS AND METHODS

(75) Inventor: Major K. Howe, 89 George Owens Rd., Abbeville, SC (US) 29620

(73) Assignee: Major K. Howe, Abeville, SC (US)

(*) Notice: Subject to any disclaimer, the term of this patent is extended or adjusted under 35 U.S.C. 154(b) by 1120 days.

(21) Appl. No.: 11/225,752

(22) Filed: Sep. 13, 2005

(65) Prior Publication Data
US 2007/0058176 A1 Mar. 15, 2007

(51) Int. Cl.
| | |
|---|---|
| G06K 9/00 | (2006.01) |
| G01N 21/86 | (2006.01) |
| G01V 8/00 | (2006.01) |
| G01B 11/24 | (2006.01) |
| G01B 11/04 | (2006.01) |
| G01B 11/08 | (2006.01) |
| G06F 19/00 | (2006.01) |

(52) U.S. Cl. .................. 382/152; 700/110; 700/122; 356/613; 356/638; 250/559.12; 250/559.24

(58) Field of Classification Search ............. 700/97–98, 700/114–119, 110, 122; 382/141–143, 152–153; 356/376, 384, 613, 638; 250/559.12, 559.24
See application file for complete search history.

(56) References Cited

U.S. PATENT DOCUMENTS

| | | | | |
|---|---|---|---|---|
| 6,055,329 A | * | 4/2000 | Mufti | .......................... 382/152 |
| 6,138,052 A | * | 10/2000 | Kristensen et al. | .......... 700/117 |
| 6,678,404 B1 | * | 1/2004 | Lee et al. | ..................... 382/155 |
| 2005/0276907 A1 | * | 12/2005 | Harris et al. | .................... 427/8 |

OTHER PUBLICATIONS

Website address: http://www.betalasermike.com; entitled: Beta LaserMike—Precision Measurement and Control Systems; printed Feb. 8, 2006; 1 page.
Website address: http://www.betalasermike.com/asp-data/pdf/diameter/hdimeasure/accuscan1000.pdf; entitled: AccuScan 1000; printed Feb. 8, 2006, copyright 2003; 4 pages.
Website address: http://www.betalasermike.com/diameter/default.aspx; entitled: BETA LaserMike—Precision Measurement and Control Systems—Diameter Measurement; printed Feb. 8, 2006; 1 page.
Website address: http://www.betalasermike.com/asp-data/pdf/diameter/hdimeasure/acuscan3000.pdf; entitled Accuscan™ 3000 Series—In-Process Diameter Measurement; printed Feb. 8, 2006; copyright 2003; 2 pages.

(Continued)

*Primary Examiner*—Matthew C Bella
*Assistant Examiner*—Nathan Bloom
(74) *Attorney, Agent, or Firm*—Thomas, Kayden, Horstemeyer & Risley, LLP

(57) ABSTRACT

A manufacturing process for sheet or shaped work products includes advancing the work product in a direction along a processing path; establishing a reference line with respect to the processing path; capturing visual data related to the work product; converting the visual data into a pixel array; and setting a predetermined line of pixels to correspond with the reference line.

16 Claims, 29 Drawing Sheets

OTHER PUBLICATIONS

Website address: http://www.betalasermike.com/asp-data/pdf/diameter/hdimeasure/holix.pdf; entitled Holix Series—High-Speed Diameter Measurement & Scanning Flaw Detection; printed Feb. 8, 2006; copyright 2004; 2 pages.

Website address: http://www.betalasermike.com/asp-data/pdf/diameter/hdimeasure/benchmike.pdf; entitled BenchMike 283 Series—Benchtop Laser Micrometer; printed Feb. 8, 2006; ISO 9001 Certified; 4 pages.

Website address: http://www.betalasermike.com/length/default.aspx; entitled: BETA LaserMike—Precision Measurement & Control Systems; printed Feb. 8, 2006; 1 page.

Website address: http://www.betalasermike.com/asp-data/pdf/length/hdimeasure/ls4000_series_brochure.pdf; entitled LaserSpeed—Non-Contact Speed & Length Gauge—LS4000 Series; printed Feb. 8, 2006; copyright 2005; 4 pages.

Website address: http://www.betalasermike.com/asp-data/pdf/length/howdoi/Stretch%20Draw%20Control%20Measurement.pdf; entitled Application Note—Stretch/Draw Control with the LaserSpeed 4000; printed Feb. 8, 2006; 2 pages.

E-mailed newsletter (http://www.globalspec.com/newsle3tter/ViewIssue?Vol=Vol6Issue6B&Pub=1) from Global Spec; entitled: Techs & Specs: Dynamometers, Frame Grabbers, Optical Comparators and more; Feb. 7, 2006—vol. 6 Issue 6B; printed Feb. 8, 2006; 6 pages.

* cited by examiner

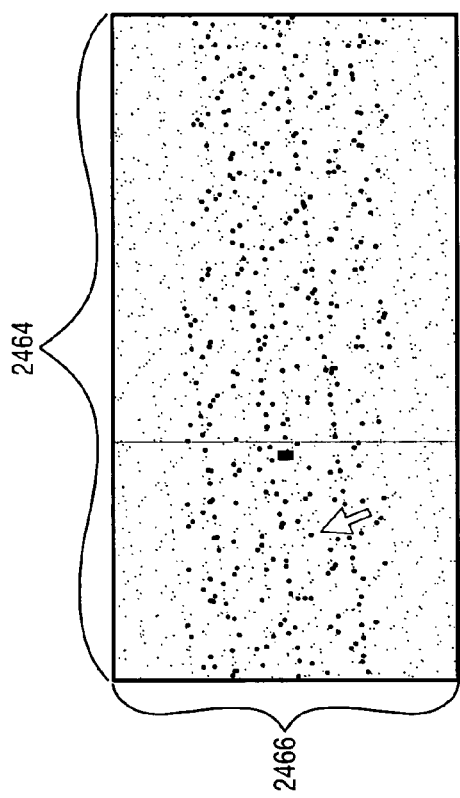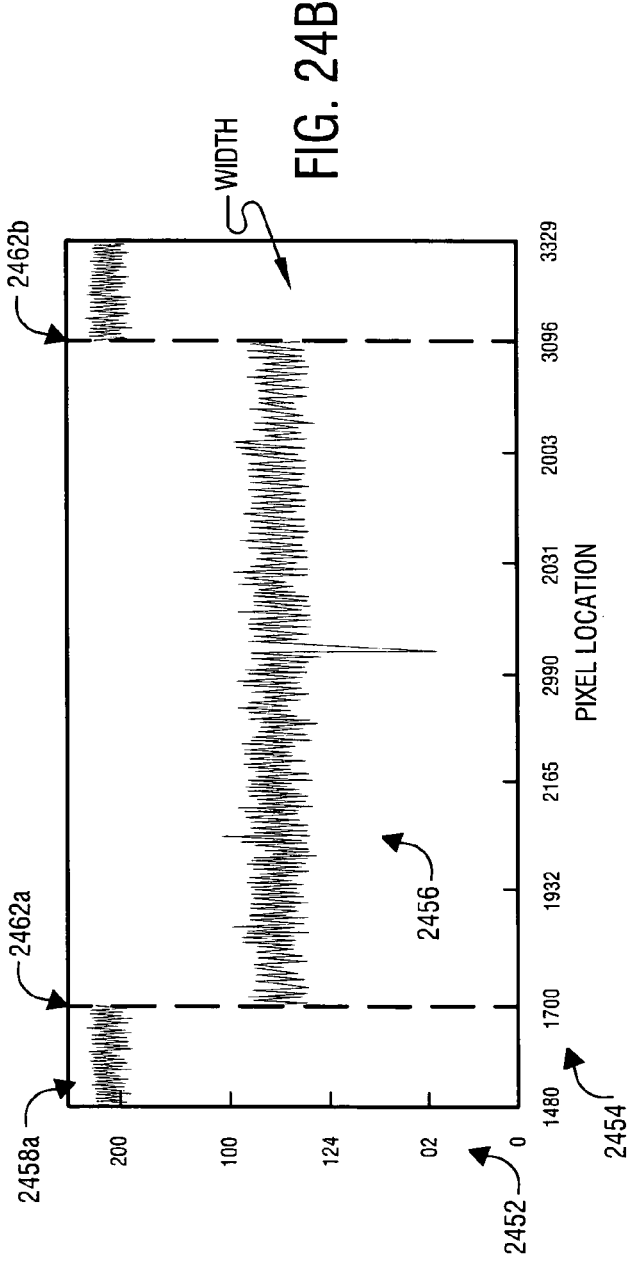
FIG. 24A
FIG. 24B

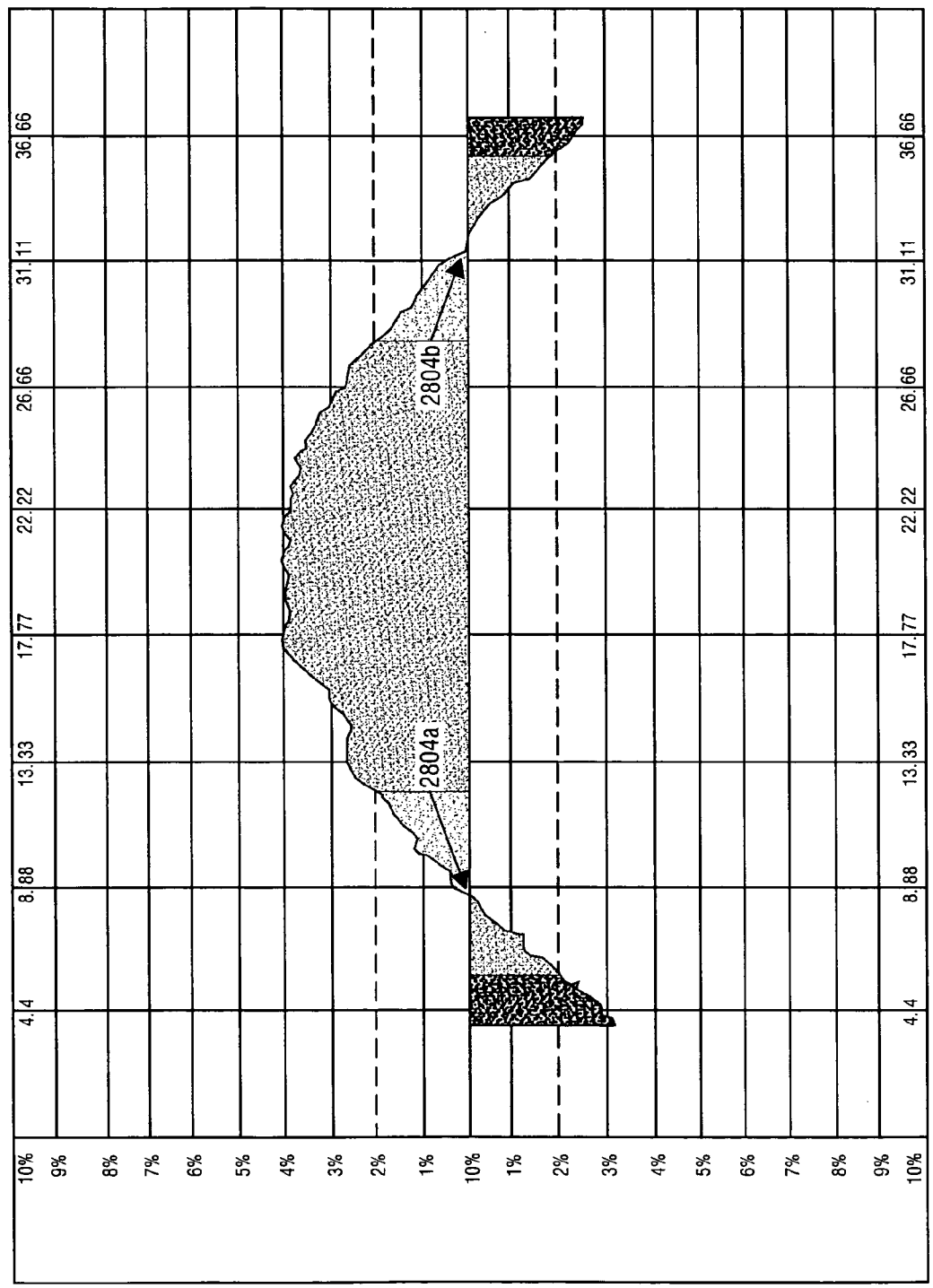

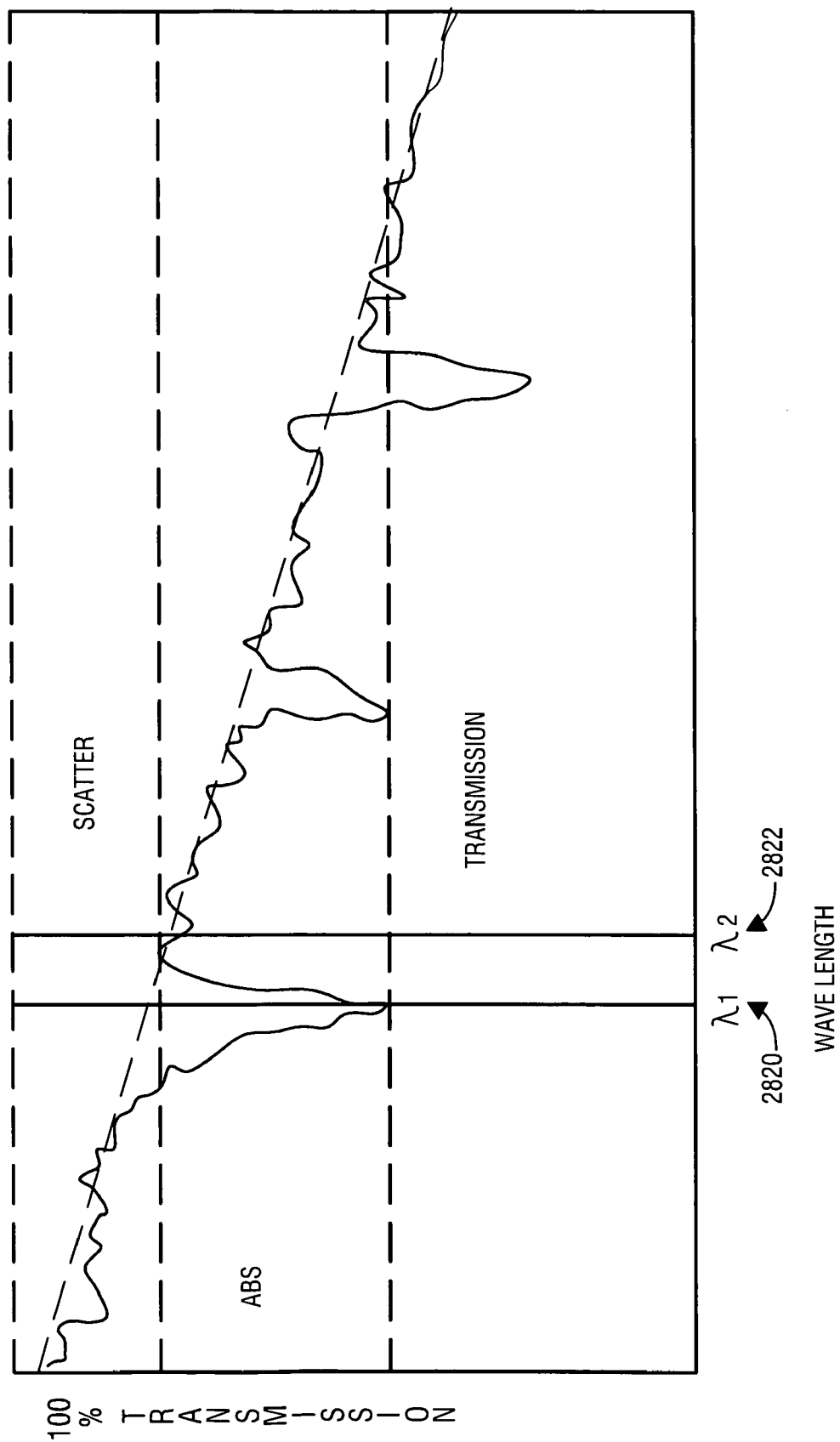

PIXEL POSITIONING SYSTEMS AND METHODS

TECHNICAL FIELD

The field of this disclosure relates to a detection and control system for the continuous manufacture of work products including sheet material and/or geometrically shaped structural products. More specifically, this disclosure relates to systems and methods for pixel positioning on the products.

BACKGROUND

Continuously manufactured products, can include profile shapes and web materials. Profile shapes may take many forms such as tubing, hose, pipe, and plastic lumber with dimensions such as 2×4's and 4×4's, while web materials are typically a continuous sheet of material of a given width. Profiled shaped materials can be any shape, but are usually elongated products with cross-sections that are generally square, rectangular, or circular. Looking down the length of the product, the profile shape can have four walls that define a square (or rectangle), with a hollow center. The opposing walls generally will have equal cross sectional lengths and each wall will usually have an equal thickness measured from the inside surface of the wall to the outside surface or outer periphery of the wall.

For example, 4×4 extruded polymer lumber may be of any length, but the width and depth are generally both 4 inches, measured about the perimeter. Thus, the product has four sides that are all equal in length (hence 4×4), and each side has a thickness (which is generally uniform for all the walls).

A continuously formed product with a shaped profile generally begins in liquid form (or amorphous solid) as a result of heating in an extruder. The raw material is introduced to the extruder in pellet form. An exit orifice of the extruder includes a center shape called a mandrel and an adjustable outer ring called a die. These two objects can have a discernable space between them and the extruder injects the liquefied product material through the space. When the liquefied product is properly cooled, it can form a desired shape of the final work product. The mandrel can define the inner walls of the product and the die can define the outer walls of the product. As the desired shape is acquired, the amorphous solid material can be sent into a cooler for hardening.

The work product can move through these operations by use of a pulling device. The pulling device can be located toward the end of the manufacturing process, and can pull the hardened product down the processing line. One concern in this process is maintaining a desired shape and wall thickness for each side of the product. Wall thickness can be increased or decreased by changing the speed of the pulling device. Similar to stretching a piece of bubble gum, by increasing the speed of the pulling device, the amorphous portion of the product will typically stretch, thereby reducing the wall thickness of the final product. Alternatively, slowing the pulling device speed can increase the wall thickness of the final product.

While the pulling device has the ability to increase or decrease the wall thickness by changing speed, a pulling device can generally only simultaneously change the thickness of all sides of the product. Therefore, if one side has an appropriate thickness, but another side does not, the pulling device will generally be of little value. Similarly, measuring the wall thickness can be a difficult task, as many measuring devices require contact with the product, and others do not provide accurate readings.

Web materials can be made of any of a plurality of materials including paper, plastic, carpet, or other materials. Web materials (as well as shaped profiles) may have a plurality of different components that need measurement and adjustment for quality control and cost management. These components can include length control, width control, wall thickness control, coating thickness control, film thickness control, and opacity control.

Historically, nuclear measurement devices, ultra sonic sensors have provided measurement and control of the dimensions of continuously formed work products such as web materials and shaped profiles. While these techniques can have benefits, they also have drawbacks. With shaped profiles, this measurement is generally taken on cylindrical pipe and some non-cylindrical tubing because of the symmetry of the products. Shaped profiled work products that have sharp angles and several sides, such as continuously formed lumber products, do not easily lend themselves to sensors that usually contact the product to measure wall thickness. Using a single sensor to measure wall thickness of any multisided object usually can be unreliable. In addition, contact by the sensor against the surface of the product has the potential to alter the position or shape of the product, thus decreasing the sensor's accuracy.

Additionally, there is often difficulty in the manufacturing process due to misplacement of the die with respect to the mandrel. This can result in varying wall thickness of each side of the work product. As stated above, work products having continuously manufactured walls of different thickness usually renders the pulling device unable to effectively correct wall thickness errors.

Further, additional problems can occur during other types of production activities. With continuously manufactured products, such as sheet materials and shaped profiles, defects may exist on the material during manufacture. The defects can occur in any of a variety of ways including dimension defects, coating thickness defects, film thickness defects, and opacity defects. One problem that exists is locating the irregularity of the work product so that a correction to the production process can be made Thus, a heretofore unaddressed need exists in the industry to address the aforementioned deficiencies and inadequacies.

SUMMARY

One embodiment discussed in this disclosure includes size detection and control method of a work product in a manufacturing process. This embodiment includes advancing a work product in a direction along a processing path; determining a reference line with respect to the processing path; capturing visual data related to the work product; converting the visual data into a pixel array; and setting a predetermined line of pixels to correspond with the reference line.

Also included in this disclosure is a system for manufacturing a shaped profile material. One embodiment of this system includes a mandrel and a die that are configured to define the boundaries of a shaped profile. The system also includes a visual data capture device configured to capture visual data from the material, and first logic configured to convert the visual data from into a pixel array. Finally, a material advancing device is included and configured to advance shaped profile material in a direction along a processing path.

Other systems, methods, features and/or advantages will be or may become apparent to one with skill in the art upon examination of the following drawings and detailed description. It is intended that all such additional systems, methods, features and/or advantages be included within the scope of the present invention and be protected by the accompanying claims.

BRIEF DESCRIPTION OF THE DRAWINGS

The components in the drawings are not necessarily to scale relative to each other. Like reference numerals designate corresponding parts throughout the several views.

FIG. 24A is a screenshot of a typical work product, as illustrated in FIG. 2

FIG. 24B is a screenshot of a typical line camera scan of the work product from FIG. 24B.

FIG. 28A is a screenshot diagram of output data from a nuclear gauge scanning the width of a moving work product that can be taken from the system from FIGS. 27A, 27B, 27C.

FIG. 28B is a sketch of an infrared spectrograph related to the measurement techniques illustrated in FIGS. 27A, 27B, 27C.

DETAILED DESCRIPTION

Figure 1:
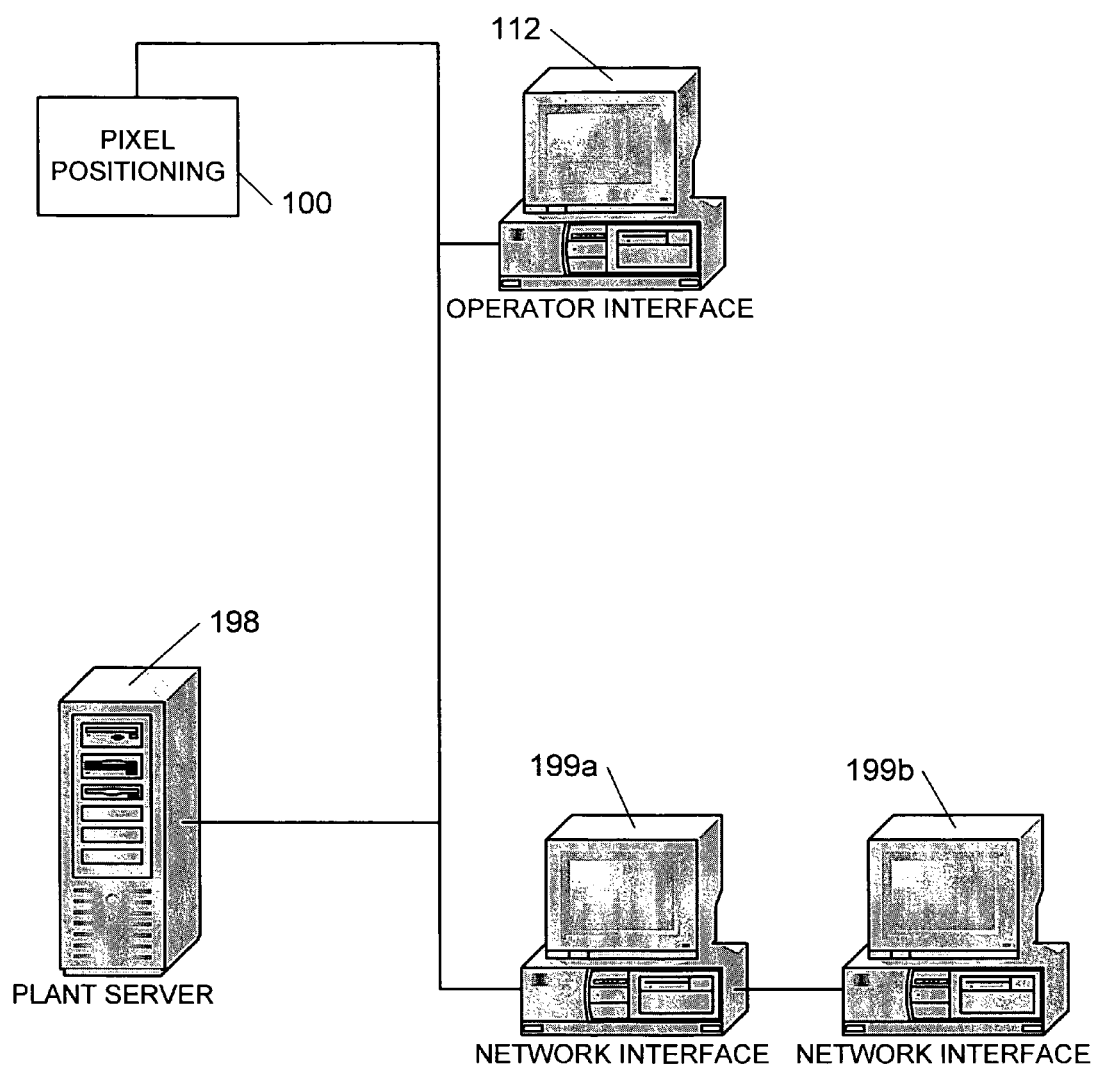
FIG. 1 is a functional block diagram illustrating interconnectivity of a pixel positioning integrated in a network environment.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views. While several embodiments are described in connection with these drawings, there is no intent to limit the disclosure to the embodiment or embodiments disclosed herein. On the contrary, the intent is to cover all alternatives, modifications, and equivalents.

FIG. 1 is a functional block diagram illustrating interconnectivity of a pixel positioning system integrated in a network environment. More specifically, an operator interface 112 can be coupled to a pixel positioning system 100. Data may be communicated via an internal (or external) network such as Ethernet to the operator interface 112. The operator interface can be coupled to a Dynamic Data Exchange (DDE) or Transmission Control Protocol/Internet Protocol (TCP/IP) interface. Also coupled to the operator interface 112 may be a plant server 128, which may be coupled to at least one network interface 132a, 132b.

Figure 2:
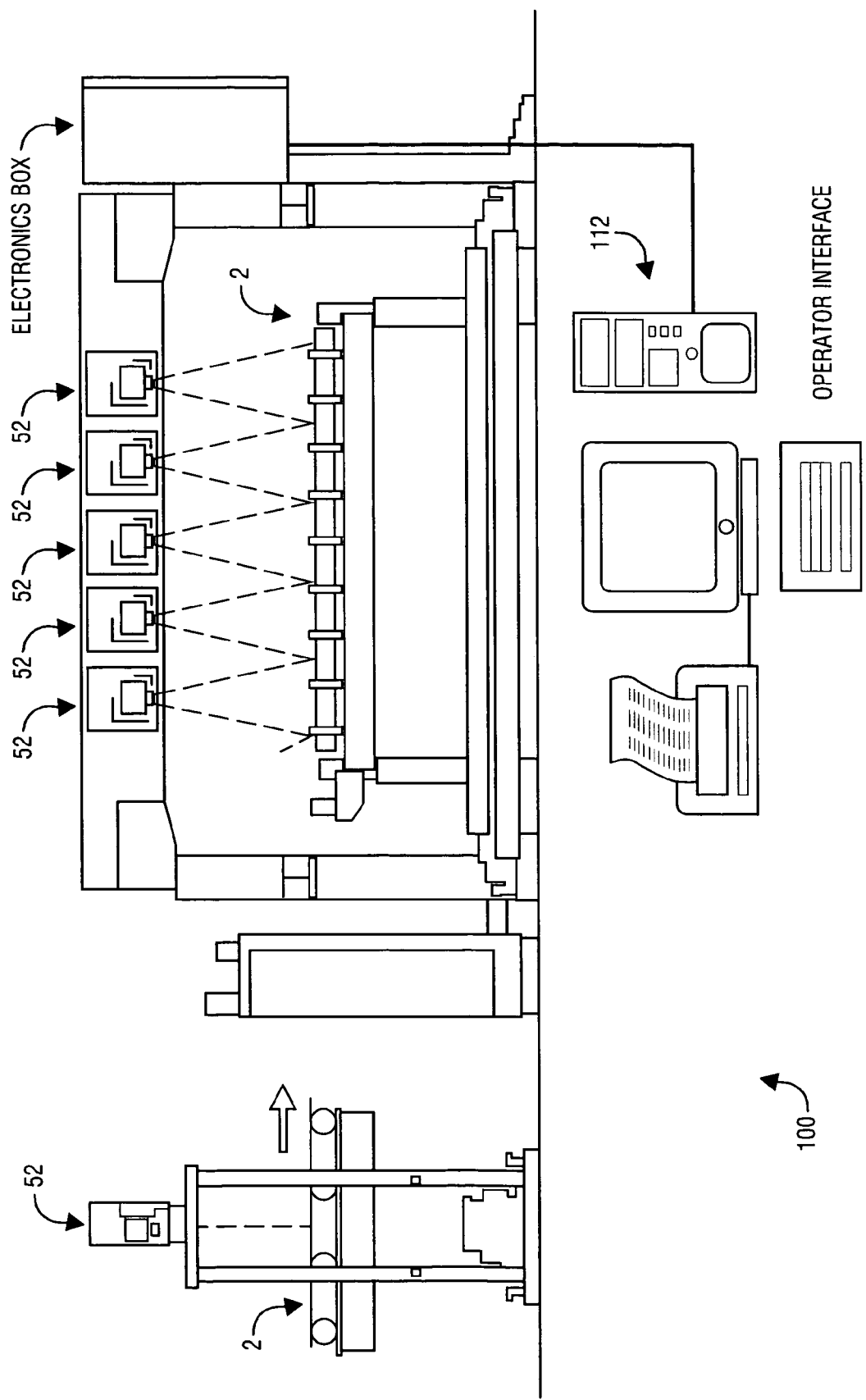
FIG. 2 is a system for manufacturing continuously produced work products, which can be integrated in the system from FIG. 1.

FIG. 2 is a system for manufacturing continuously produced work products, which can be integrated in the system from FIG. 1. As illustrated, system 100 includes a plurality of visual data capture devices 52. The video capture devices 52 can include line scan cameras taking pictures of a transmitted light through a work product 2. The visual capture devices 52 can take pictures at any rate desired for the particular manufacturing process. One visual data capture speed commonly implemented is around 10 to 20 times per second. While FIG. 2 illustrates an embodiment with a plurality of visual capture devices, it is common to have a single camera with around 5000 pixels in a one-line array that will be processed at a rate of around 60 MHz. This translates to each pixel being processed 12 times per second. As the work product 2 moves along the manufacturing path, illustrated by the arrow from left to right, the visual data capture devices can capture data related to various properties of the work product including defects, abnormalities, and dimensions.

Figure 3:
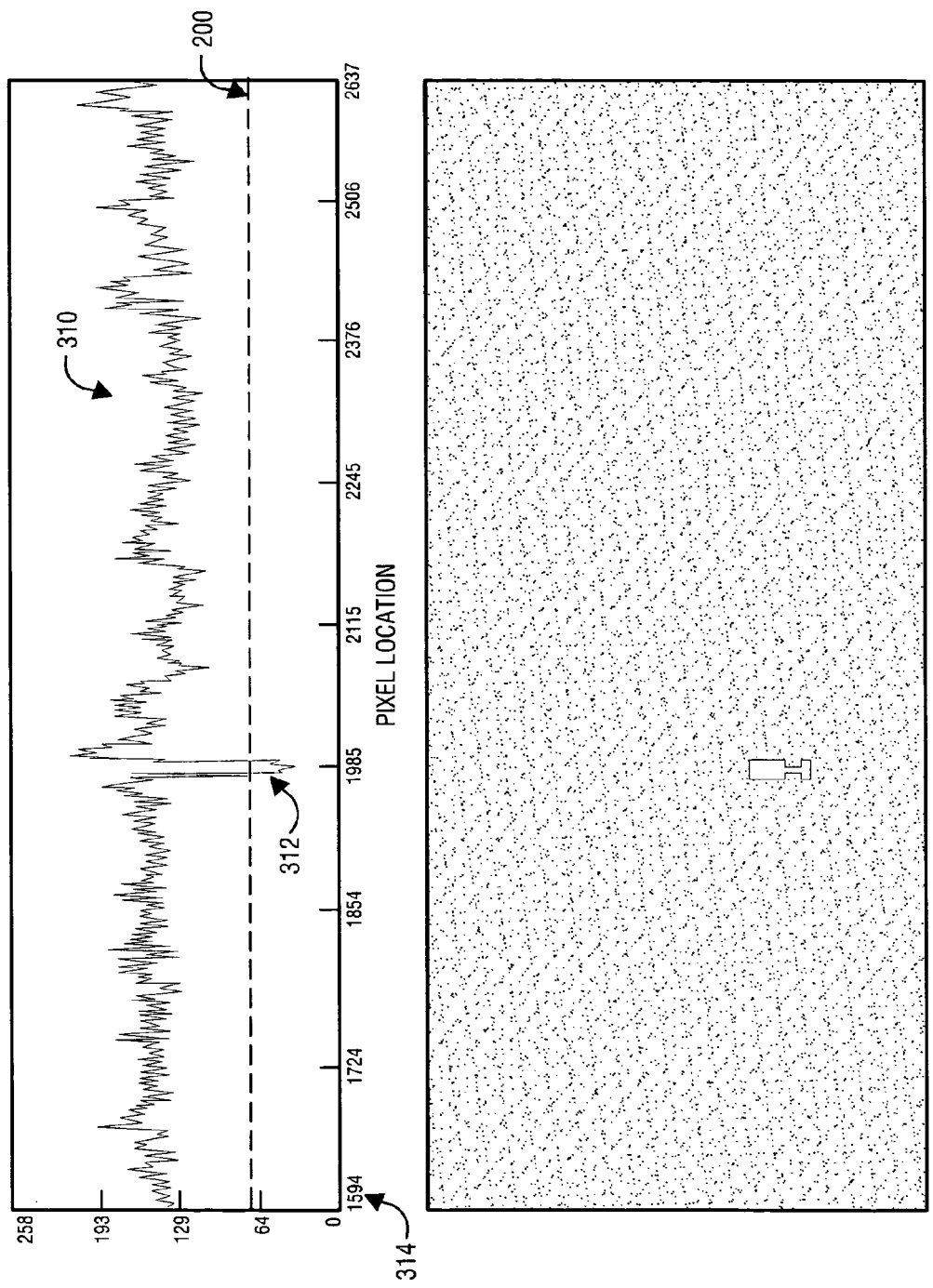
FIG. 3 is an output data graph that may be produced during manufacturing continuously produced work products from systems such as those from FIG. 2.

FIG. 3 is an exemplary output data graph that may be produced when manufacturing continuously produced work products from systems such as those from FIG. 2. As illustrated, the data can include a line graph 310 representing any of a plurality of data. In at least one embodiment, the line graph 310 illustrates the transmissivity of a work product. A lighting signal can be communicated to the work product, and changes in the intensity of the light signal typically result when the light signal is reflected/refracted from the defect in the material. In the graph at the top of the page, the x-axis 314 represents a pixel number associated with the visual data capture device from FIG. 2. The y-axis 314 is displayed in arbitrary units called a gray scale. In this nonlimiting example, if the material is completely opaque the line graph 310 can have a value of "0". If there is 100% transmission then the line graph can have a value of 256.

As a nonlimiting example, the following information can be derived from FIG. 3. First, if the work product is 60 inches wide, then the defect 312 can be found at approximately (1990/5000)×60 or 23.88 inches from the edge. Additionally, if line speed is also being accumulated, the exact location of the defect can be determined and mapped in any given roll of work product materials produced.

One should note that the system could include other more advanced logic features that have a different role. One of these advancements can be referred to as uniformity or formation analysis logic. This logic can be configured to compare the uniformity of one given area to another on the same web. The purpose is to compare the consistency of one area to its counterpart in another part of the work product. A nonlimiting example would be to compare the consistency of bond paper to the blotchiness of kraft paper.

An additional variation of a comparator technique is called pattern recognition. In the case of repeating patterns such as wallpaper or other printing patterns, the system can be configured to recognize the desired pattern of light and compare that to any upcoming pattern and detects any differences.

Figure 4:
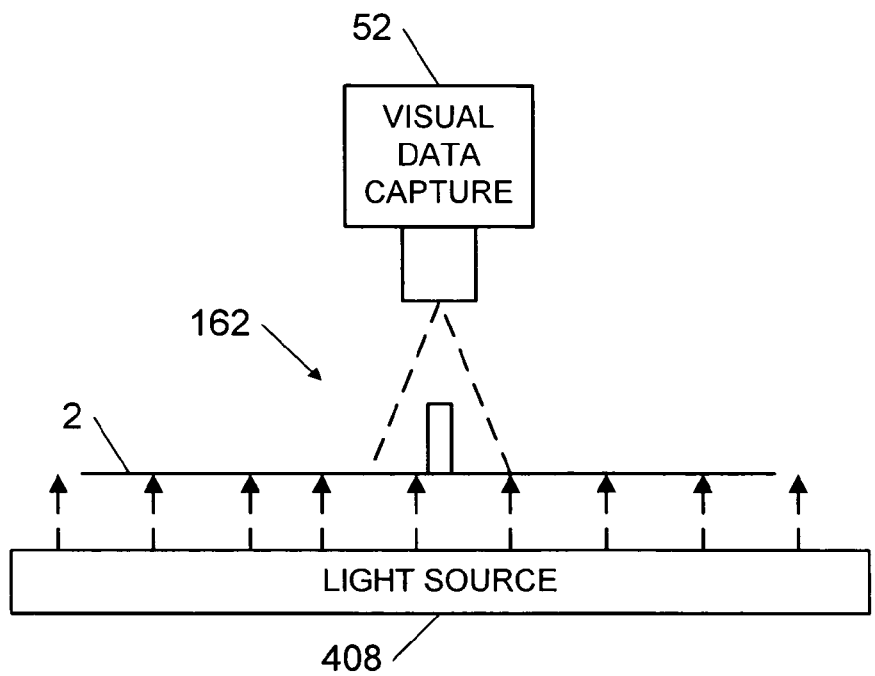
FIG. 4 is a functional diagram illustrating one approach for capturing data in manufacturing continuously produced work products, as shown in FIG. 2.

FIG. 4 is a functional diagram illustrating one approach for capturing data in manufacturing continuously produced work products, as shown in FIG. 2. As illustrated, visual capture device 52 is illustrated as residing directly above, and directed in an orthogonal direction as the work product 2 is moving out from the page. A light source 408 is located opposite the work product 2 from the visual capture device 52, and can be configured to emit a light toward the work product 2. Depending on the particular implementation and work product being manufactured, this light will cause the work product 2 to cast a shadow, which visual capture device 52 can perceive. Alternatively, if the work product 2 is at least partially translucent, the light source can emit a light signal that shines through the work product 2. The light signal can then be perceived by visual capture device 52. In either event, the visual capture device 52 can capture data related to the defect 162 located on the work product 2.

Figure 5:
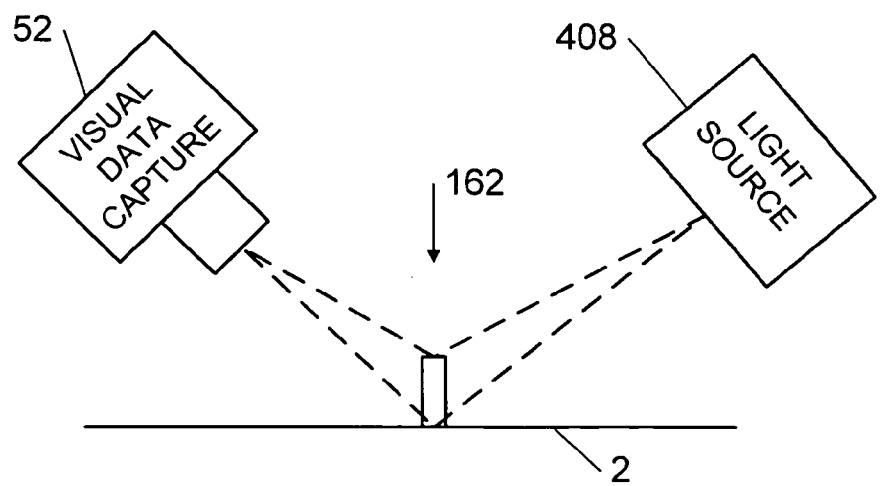
FIG. 5 is an alternate functional diagram illustrating another approach for capturing data in manufacturing continuously produced work products, as shown in FIG. 2.

FIG. 5 is an alternate functional diagram illustrating another approach for capturing data in manufacturing continuously produced work products, as shown in FIG. 2. Similar to FIG. 4, this nonlimiting example includes a visual capture device 52, a work product 2 and a light source 408. However, in this nonlimiting example, the light source 408 is located at an angle from the visual capture device 52. The light source is directed to emit a light signal to the work product 2 such that the light signal is reflected from the work product 2, and captured by the visual capture device 52.

As is evident to one of ordinary skill in the art, the angle of reflection depends on the type of work product 2 being produced. Depending on the work product 2, a system operator may desire an adjustment of the relative positions of these components.

Wall Thickness and Shaped Profiles

Consider that an extruder can have a die that defines an opening that forms the exterior shape of a work product and a mandrel that is fixed in the space of the die and never moves relative to the die. The mandrel defines a center void in the work product and can determine the inner dimensions of the product. If the same mandrel is used, the inner dimensions will always remain the same. Therefore, some of the variables typically in the extrusion process are the concentricity of the die ring with respect to the mandrel and the take away speed of the inline-pulling device.

As is evident, when the die is not correctly aligned with the mandrel, the finished product can have an asymmetric shape. Further, the thickness of each wall of the work product will likely vary with respect to the thickness of the other walls. Therefore, a method of accurately setting the die is desired.

One method of setting the die implements the use of pixel arrays. At one or more points along the manufacturing process described above, a first measuring device may be used to measure the width of a side of the product. In one embodiment, the first measuring device may have a light source that shines on the material, casting a shadow of the product. On the opposite side of the product is a sensing device, centered on the longitudinal axis of the mandrel. The sensing device can receive and digitize the shadow into a pixel array. Because the center pixel of the pixel array is centered on the mandrel, the sensing device can count the number of pixels from the center pixel line to the edge of the shadow in each direction. If the number of pixels in one direction do not equal the number of pixels in the other direction, the die is off-center in at least one direction. Additionally, if the die is "twisted" with respect to the mandrel, the number of pixels consumed by the shadow can be greater than the desired pixel count. This data allows the system to determine when the die needs to adjustment.

A second measuring device may also be used to measure an alternate side of the product using the same technique. The number of measuring devices in the system may vary, depending on the shape and number of sides on the product. Additionally, reflection techniques and even photographic or video data may also be implemented to allow the sensing device and the light source to be located on the same side of the product.

As a nonlimiting example, with reference to a 4×4, if one were to shine a light source onto one of the vertical surfaces of the product, the product would cast a shadow. The sensing device could detect and convert the shadow into a pixel array.

By counting the number of pixels consumed by the shadow in the vertically up direction and by also using a similar shadow in the horizontal axis and comparing the number of pixels consumed by the shadow in the horizontal direction, the operator can determine if the die is centered with respect to the mandrel.

One should also note that pixel counting is not limited to counting along the center pixel or reference line. As is evident, counting at different or even multiple pixel lines may provide more information as to correcting the die placement.

One should also note that pixel arrays can be captured by differing techniques, such as a photographic lens, or a television CRT or LCD. These devices could be described as an area array. There are also line scan cameras that use an array of pixels in a contiguous straight line. These devices can be used on continuing processes such as web products to determine flaws and other anomalies. If an operator stays within the same given area, he can move the centerline of any object a precise distance by counting the correct pixels in the X and Y direction and placing the same object in a precise new location.

In one embodiment, each dimension of light could be covered by a camera with 5000 pixels and would scan at a rate of approximately 10 times per second. Using a 4×4" extruded post as an example, the resolution of the horizontal and vertical dimensions are compared with the reference line of (the line of pixels denoted as (x, 2500)). The operator can first check his screen to determine if the die was centered. If the shadow was not equidistant on both sides of the centerline, then the die can be centered around the mandrel or true reference line and could show each shadow to be equidistant about the known reference line after completion.

A remaining variable is the actual wall thickness of the product. As stated above, wall thickness can be determined by the speed of the pulling device. Therefore, the proper control of the pulling device can result in the correct wall thickness. Typically, the pulling device includes two tractor treads around the cooled product controlled by a variable speed motor. Faster speeds reduce the wall thickness and slower speeds increase the wall thickness.

Once the die is centered, wall thickness, and therefore width and depth of the product are measured. With the die centered, one can determine the length of each side of the profile by counting pixels, as described above. One method described here takes the length of each side and multiplies them together. If the calculated value does not equal the desired value, then the operator can speed up or slow down the pulling device.

For example, in the case of a 2×4 product, the method can measure the width and height of the product, and can multiply the two measurements together to achieve a calculated value. Next, the method compares the calculated value with a desired value (in this case the desired value is 8, which is 2 times 4). If the calculated value is less than 8, then the wall thickness is less than desired and the pulling device needs to slow down. If, on the other hand, the calculated value is greater than 8, then the wall thickness is too large and the pulling device needs to speed up. As is evident, the simplification of correcting the product thickness is not constrained to the multiplication of the two measurements. Any manipulation of the readings from the sensors may be implemented to more easily adjust the product thickness.

Figure 6:
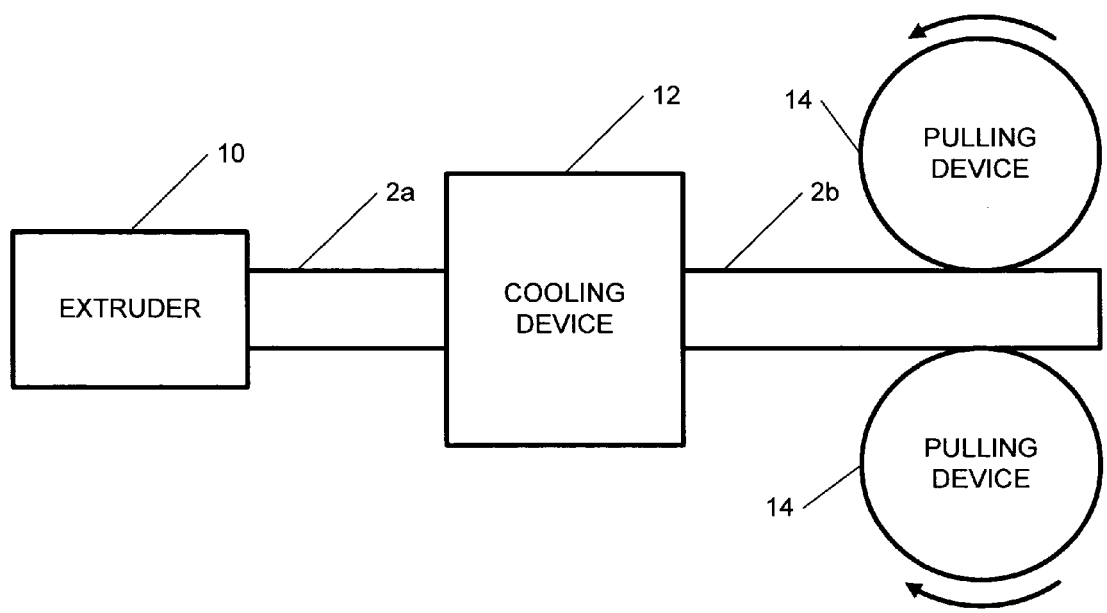
FIG. 6 is a functional block diagram of one embodiment of a system for manufacturing shaped profiled materials, similar to the system from FIG. 2.

Referring now to the drawings, FIG. 6 is a functional block diagram of one embodiment of a system for manufacturing work products, such as shaped profiled materials. As illustrated in FIG. 6, the system includes an extruder 10 for shaping the liquefied or amorphous solid material into the desired shaped profile. The extruder 10 includes a mandrel 24 and a die 22 (see FIG. 7) that receive the liquefied material and produce continuously manufactured product 2a, 2b, shaped in the desired shaped profile. Once shaped in the extruder 10, the uncooled continuously manufactured product 2a is sent to the cooling device 12. While the uncooled continuously manufactured product 2a may be in a substantially solid state, the cooling device 12 ensures the shape of the uncooled continuously manufactured product 2a, as defined by the extruder 10.

Also included in this embodiment of a system of manufacturing shaped profiles is a pulling device 14. The pulling device 14 is configured to advance the continuously manufactured product 2a, 2b from the extruder 10 and the cooling device 12 to other stations in the manufacturing process. The pulling device 14 is configured to pull the continuously manufactured product 2a, 2b from the cooler. Additionally, since the cooled continuously manufactured product 2b is coupled to the uncooled continuously manufactured product 2a, the pulling device 14 can also act as a thickness determination device. The faster the pulling device 14 pulls the cooled continuously manufactured product 2b, the thinner the uncooled continuously manufactured product 2a will stretch. Similarly, the slower the pulling device 14 pulls the cooled continuously manufactured product 2b, the thicker the uncooled continuously manufactured product 2a will remain.

The pulling device 14 of FIG. 6 includes two cylindrical rollers to pull the cooled continuously manufactured product 2b. One should note that this is but a nonlimiting example of one type of pulling device. As is evident to one of ordinary skill in the art, any type of pulling device may be used to achieve the same result. Similarly, other additions, deletions, and variations of the system disclosed in FIG. 1 are also included in this disclosure. FIG. 6, as with all examples in this disclosure are intended to illustrate, and not to limit.

Figure 7:
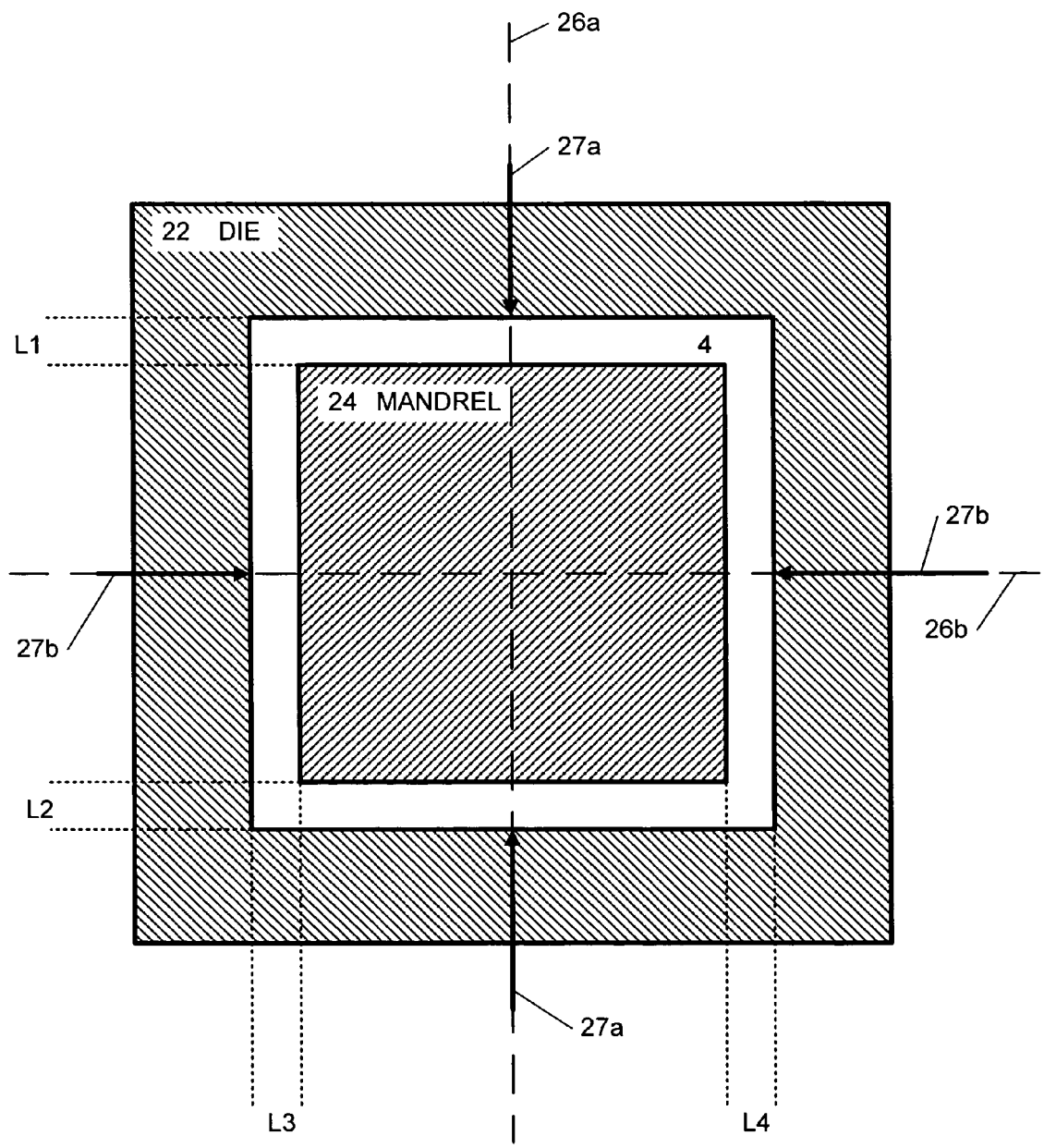
FIG. 7 is a functional block diagram of one embodiment of a mandrel and die, located in the system of FIG. 6.

FIG. 7 is a functional block diagram of one embodiment of a mandrel and die, located in the system of FIG. 6. As discussed with reference to FIG. 6, the extruder 10 includes a mandrel 24 and a die 22. The mandrel 24 may be of any shape, but in this nonlimiting example, the cross-section of the mandrel 24 is square, to produce a 4×4 or similar shaped profile. In some embodiments, the mandrel 24 is configured to remain stationary with respect to the rest of the system. Also included in the extruder 10 is a die 22 that defines the outer portions of the shaped profile. The die 22 may be adjustable, and is configured such that the inner portions of the die 22 are slightly larger than outer portions of the mandrel 24. The mandrel 22 may be placed in a position to define a shaped aperture 4 for the uncooled continuously manufactured product 2a to fill.

The mandrel 24 and the die 22 of FIG. 7 are aligned such that the shaped aperture 4 has equal thickness on all sides. More specifically, $L_1=L_2=L_3=L_4$. This can be illustrated by the fact that the mandrel centerline 26a matches up with die center markings 27a, and mandrel centerline 26b is in line with die center markings 27b. The mandrel centerlines 26a, 26b in this nonlimiting example are configured to mark the center of the mandrel 24. Since the mandrel 24 is stationary with respect to the rest of the system, this line should remain stationary. Similarly, the die center markings 27a, 27b illustrate the center of the die on each side. Since the die is adjustable, the die center markings 27a, 27b may move relative to the mandrel centerlines 26a, 26b.

Figure 8:
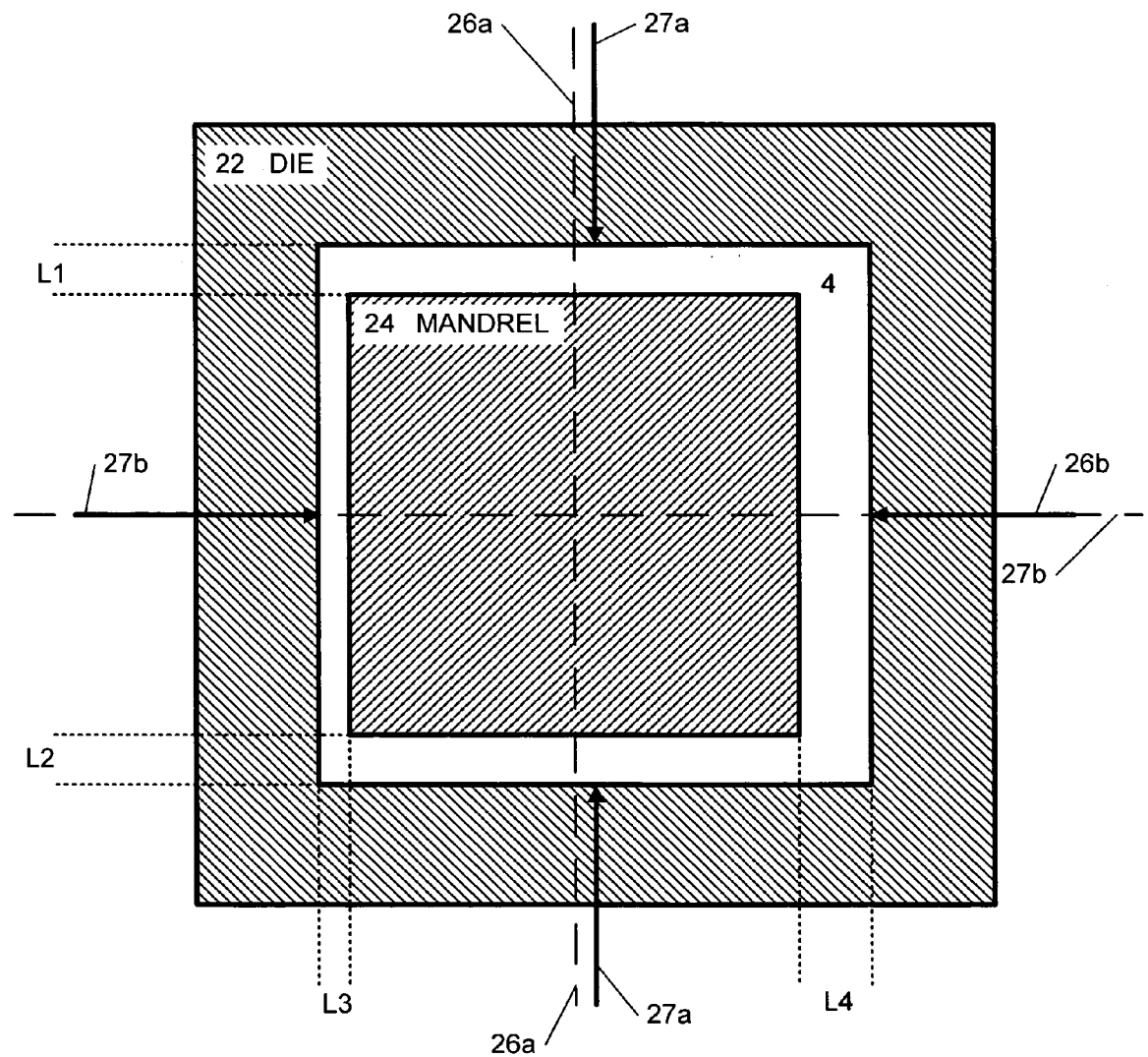
FIG. 8 is a functional block diagram of one embodiment of a mandrel and die, similar to the mandrel and die of FIG. 7, with the die out of place.

FIG. 8 is a functional block diagram of one embodiment of a mandrel and die, similar to the mandrel and die of FIG. 7, with the die out of place. As illustrated in FIG. 8, the die 22 has been shifted to the right, relative to the mandrel 24. As shown, die center markings 27a are shifted relative to mandrel centerline 26a. This scenario changes the thickness of the right and left side of the shaped aperture 4. As shown, $L_3$ is different than $L_4$. Although $L_1$ and $L_2$ are equal thickness, they have a different thickness than $L_3$ and $L_4$. Such a configuration produces a shaped profile that is asymmetrical, and in this nonlimiting example, undesired.

Figure 9:
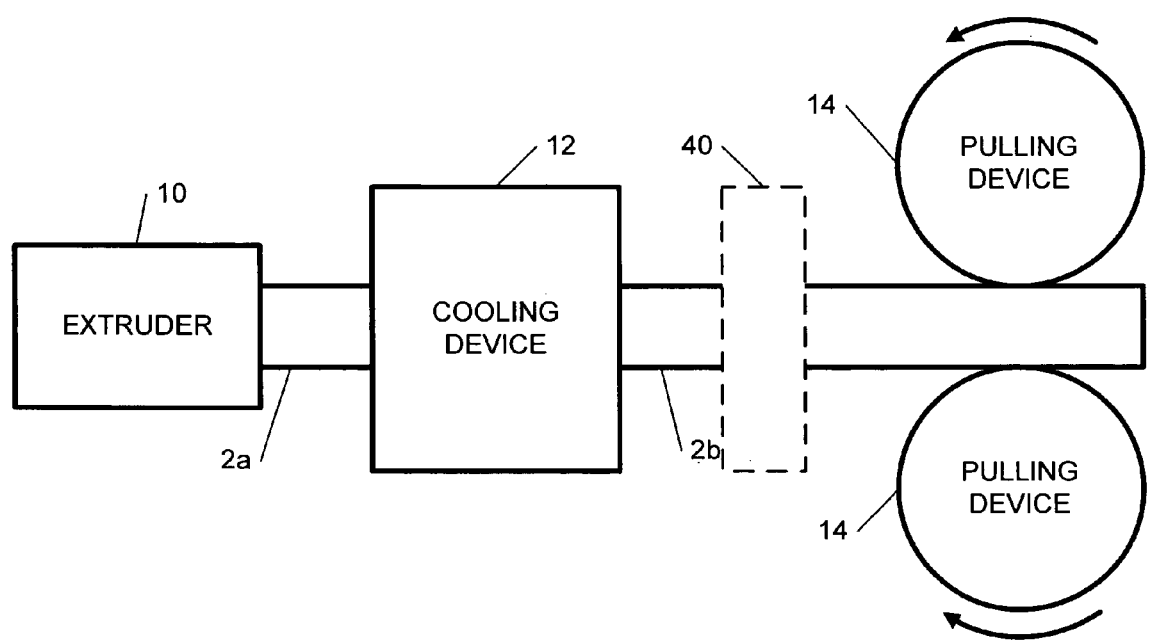
FIG. 9 is a functional block diagram of the system of FIG. 6, with a die setting system.

FIG. 9 is a functional block diagram of the manufacturing system of FIG. 6, with a die setting system 40. In at least one embodiment, the manufacturing system can be considered a first checkpoint that includes an extruder 10 to shape an uncooled continuously manufactured product 2a. Also included is a cooling device that cools the continuously manufactured product 2b. A pulling device 14 pulls the cooled portion of the continuously manufactured product 2b. In this nonlimiting example, a die setting system 40 (which may also be seen as a first checkpoint) may also be included to provide information regarding the position of the die 22. One should note that although die setting system 40 is located between the cooling device 12 and the pulling device 14, the present disclosure is not so limited. The die setting system may be placed anywhere that will achieve the desired results.

Figure 10:
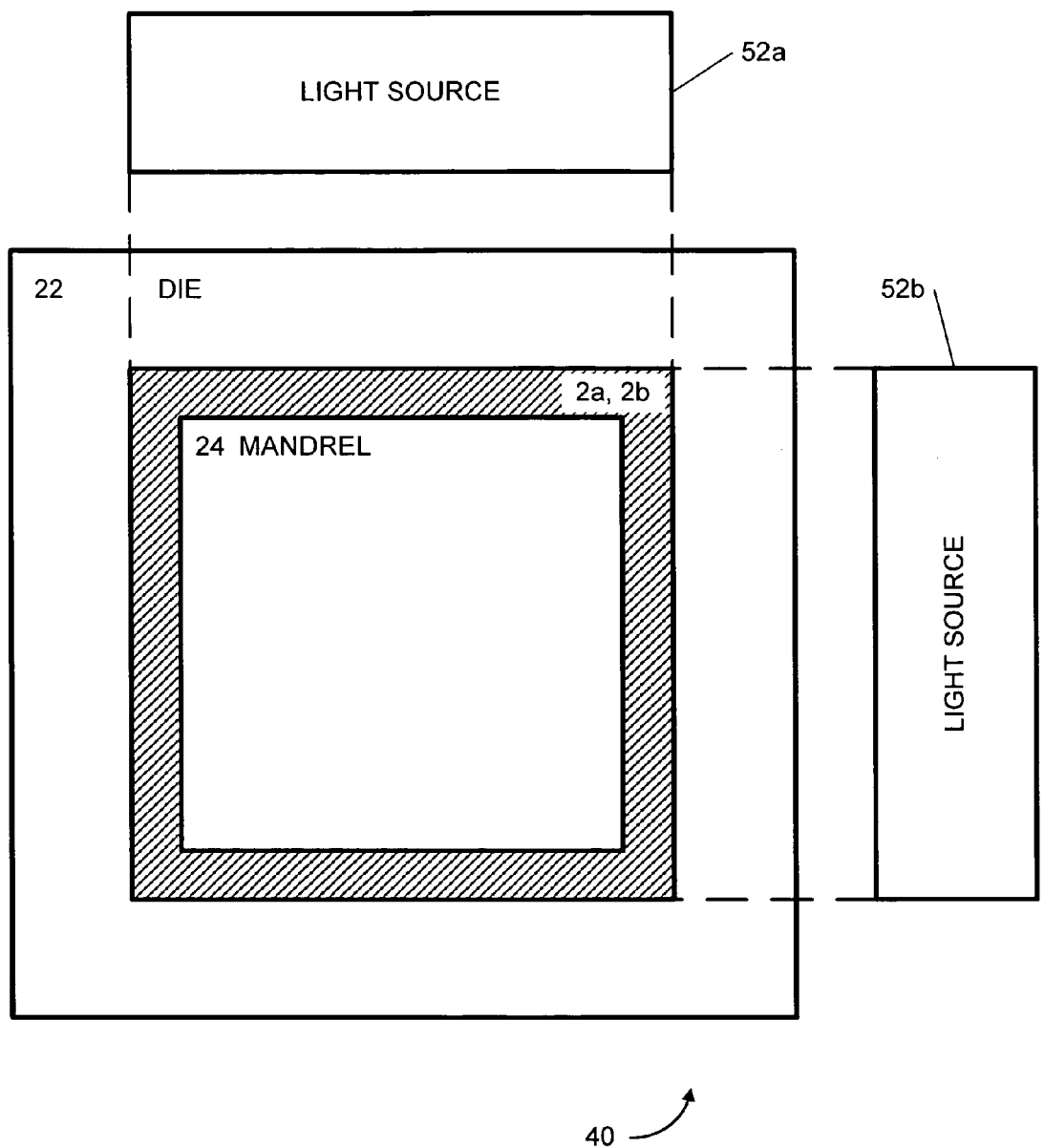
FIG. 10 is a functional block diagram of one embodiment of components that may be present in the die setting system of FIG. 9.

FIG. 10 is a functional block diagram of one embodiment of components that may be present in the die setting system of FIG. 9. The die setting system 40 of FIG. 10 includes visual data capture devices 52a, 52b positioned along two of the sides of the shaped continuously manufactured product 2a, 2b. As illustrated, the visual data capture devices 52a, 52b are configured to capture visual data regarding the position of the continuously manufactured product 2a, 2b. The visual data capture devices 52a, 52b may be any type of device capable of capturing visual data. The visual data capture devices 52a, 52b may be configured to capture light, shadow, or other similar data. In at least one embodiment, the visual data capture devices 52a, 52b include a camera and a light source positioned opposite the camera from the work product. When the light is illuminated, the camera receives visual data in the form of a silhouette of the work product. An additional exemplary embodiment of visual data capture devices 52a, 52b may include the light source being positioned on the same side of the work product as the camera. In this embodiment, the camera captures the light reflected from the light source by the work product. This reflected light may also be seen as a silhouette.

Figure 11:
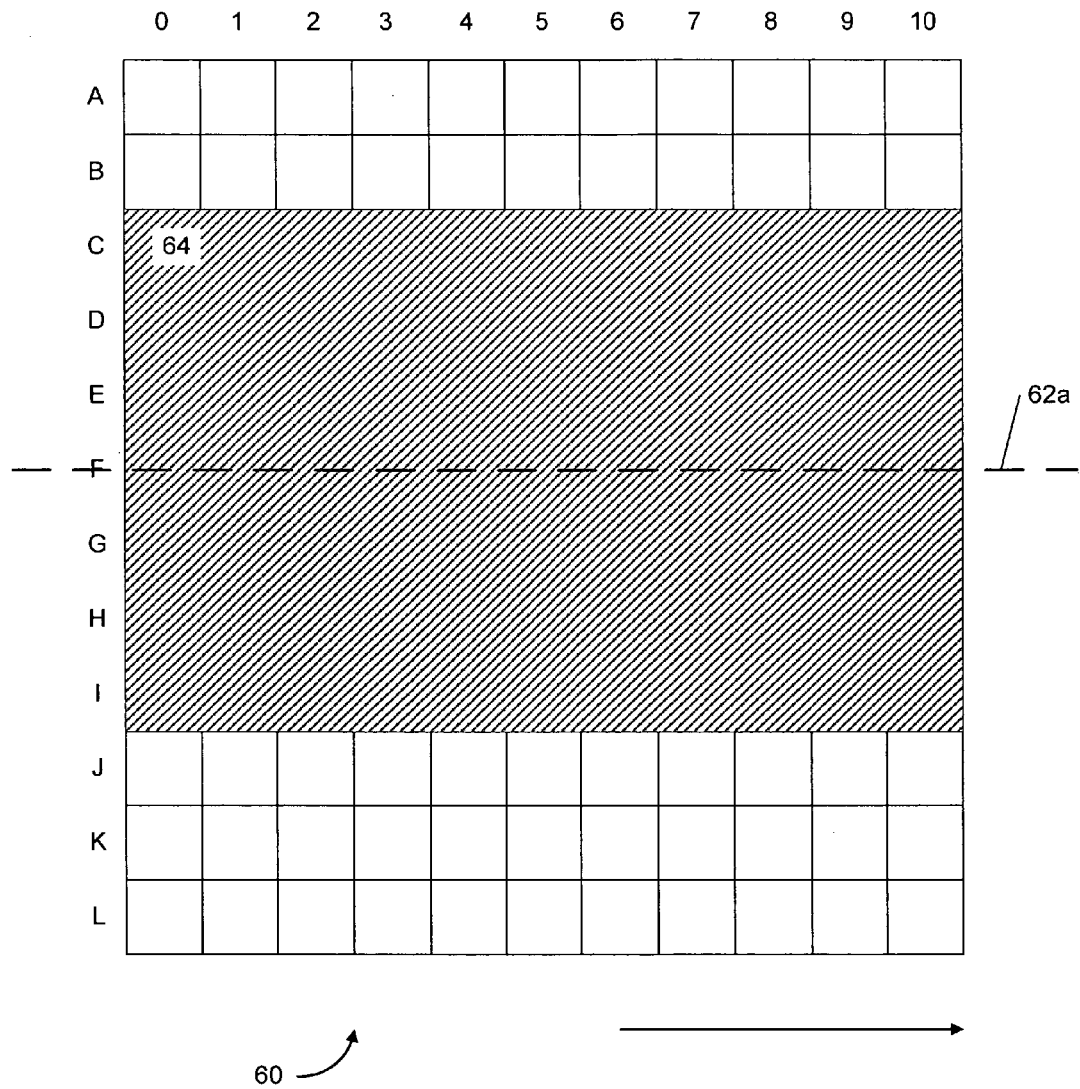
FIG. 11 is a functional block diagram of one embodiment of a pixel array that may be generated by the die setting system of FIG. 9.

The die positioning system 40 is also configured to determine at least one reference line (see FIG. 11). The die positioning system 40 is also configured to convert the visual data into a pixel array. In some embodiments, the die positioning system 40 also includes a processor for executing the functions described above.

FIG. 11 is a functional block diagram of one embodiment of a pixel array that may be generated by the die setting system of FIG. 9. The pixel array 60 of FIG. 11 illustrates possible data that visual capture devices 52a, 52b may acquire. Additionally, the die setting system 40 converts the visual data into a pixel array 60, shown in FIG. 11. Included with the pixel array is a reference line 62. This reference line 62 indicates the center of pixel array in the horizontal direction. Utilizing reference line 62 in conjunction with the shaped profile visual data 64 on pixel array 60, the system can determine whether the die 22 (FIG. 7) is out of position. If the die 22 is out of position, the pixel array 60 will include shaped profile visual data 64 that is shaded in pixels that should not be shaded except in the area defined by pixel markers C through I. If the die is out of position, pixel data other than in this region will be present. If this occurs the system can perform appropriate measures to correct the problem including, but not limited to displaying an alert to a user and providing graphics to manually or automatically adjust the position of die 22.

Although the reference line 62 of FIG. 11 is located at the center of the shaped profile visual data 64, this is but a nonlimiting example. Reference lines may be located anywhere on the pixel array to indicate a reference point by which die position can be determined. Similarly, although only one reference line 62 is illustrated in FIG. 11, any number of reference lines may be used.

Figure 12:
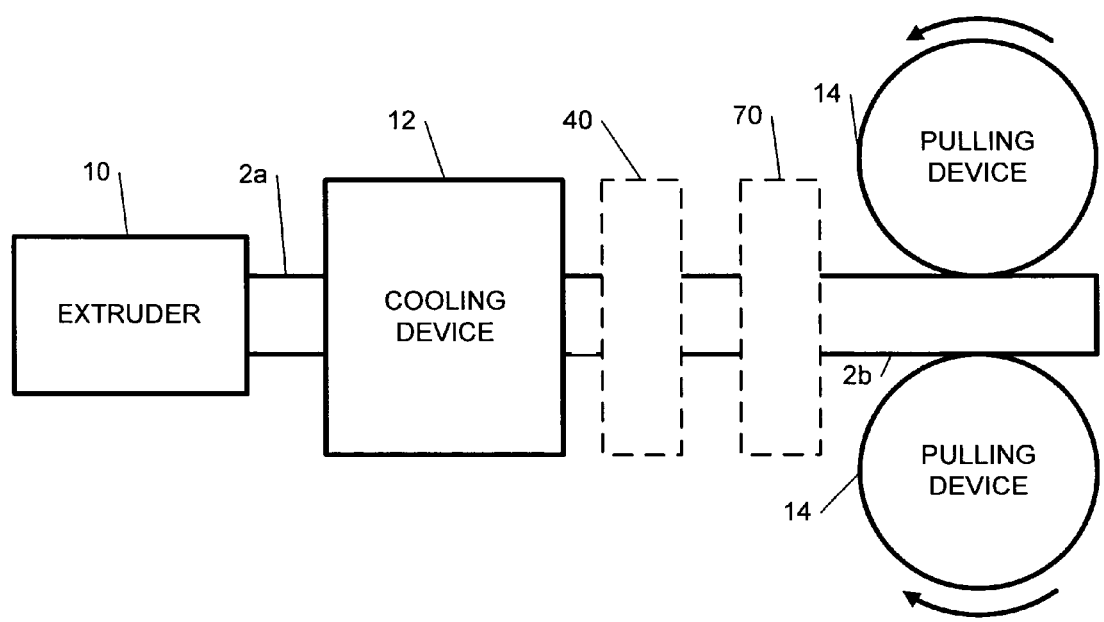
FIG. 12 is a functional block diagram of one embodiment of the system of FIG. 6, with both a die setting system and a material thickness system.

FIG. 12 is a functional block diagram of one embodiment of the system of FIG. 6, with both a die setting system and a material thickness system. Similar to FIGS. 6 and 9, the system of FIG. 12 includes an extruder 10 for shaping an uncooled continuously manufactured product 2a, a cooling device 12 for cooling the uncooled continuously manufactured product 2a, and a pulling device 14 for pulling the cooled continuously manufactured product 2b. The system of FIG. 12, however includes the die setting system 40 from FIG. 9, and a material thickness system 70 for defining a desired thickness of the continuously manufactured product 2a, 2b. One may note that although FIG. 12 illustrates a system with both the die setting system 40 and the material thickness system 70, this is but a nonlimiting example, as other embodiments may include only one of the systems. Similarly, the positions of the die setting system 40 and the material thickness system are also nonlimiting examples to illustrate one embodiment of the present disclosure.

Figure 13:
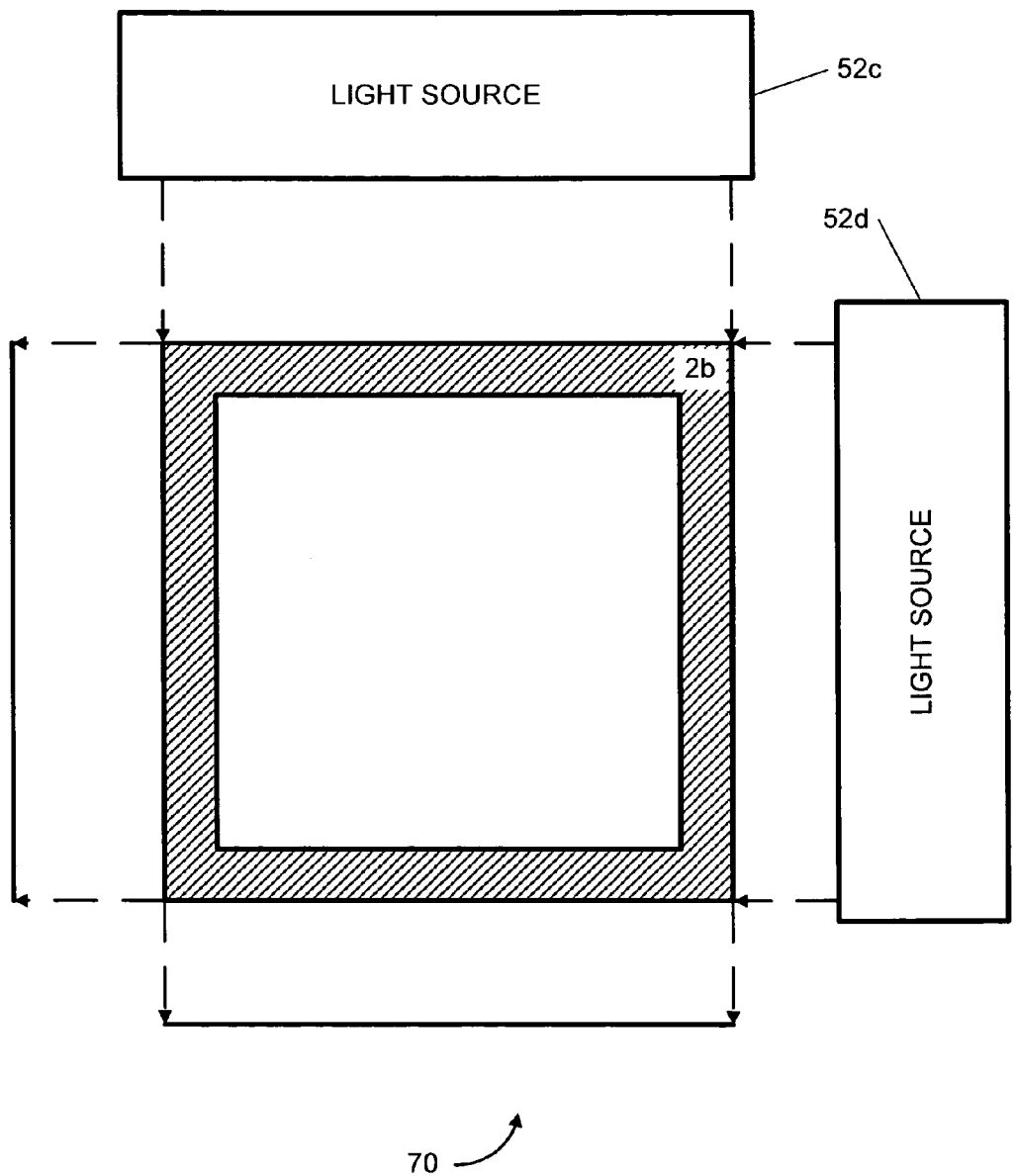
FIG. 13 is a functional block diagram of various components present in one embodiment of the material thickness system of FIG. 12.

FIG. 13 is a functional block diagram of various components present in one embodiment of the material thickness system of FIG. 12. In at least one embodiment, the material thickness system 40 of FIG. 13, can be considered a second checkpoint that includes visual data capture devices 52c, 52d that receive visual data regarding a side of the cooled continuously manufactured product 2b. The visual data capture devices 52c, 52d may be configured to capture visual data regarding a side of the cooled continuously manufactured product 2b. The visual data can then be converted to a pixel array, similar to pixel array 60, and associated with one or more reference lines, such as reference line 62. The visual data capture devices 52c, 52d may be similar to the visual capture devices 52a, 52b from FIG. 10, or they may be different, depending on their intended use.

Figure 14:
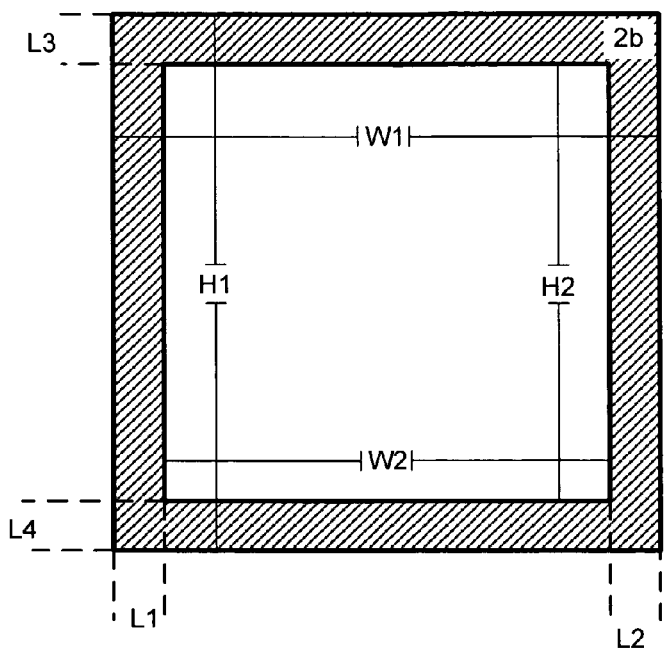
FIG. 14 is a functional block diagram of a shaped profile, illustrating computations that may be performed by the material thickness system of FIG. 12.

FIG. 14 is a functional block diagram of a shaped profile, illustrating computations that may be performed by the material thickness system of FIG. 12. The cooled continuously manufactured product 2b may be shaped with a total height equal to $H_1$, an inner height equal to $H_2$, a total width equal to $W_1$, and an inner width equal to $W_2$. Referring back to FIG. 13, the visual capture device 52d receives visual data regarding the right side of the cooled continuously manufactured product 2b. The material thickness system 70 can then convert the visual data into a pixel array, and perform calculations to determine wall thickness, $L_3$ and $L_4$. To determine the wall thickness, $L_3$ and $L_4$ the material thickness system 70 can determine the number of pixels along the height of the shaped profile visual data, as $H_1$ (see FIG. 11). The system can know the inner height $H_2$ in as the height of the mandrel 22 (see FIG. 7). By subtracting the data associated with $H_1$ from the data associated with the total height of the cooled continuously manufactured product 2b, $H_2$, the system can determine the combined thickness of $L_3$ and $L_4$. The system can then divide this value by 2 to determine the thickness of either $L_3$ or $L_4$. Similarly, using a similar technique, the thickness of $L_1$ and $L_2$ may also be determined.

One should note that since the die was adjusted to assure equal thickness of each side of the continuously manufactured product 2a, 2b, one can infer that $L_1=L_2=L_3=L_4$. Therefore, by subtracting $H_1$ from $H_2$, and dividing by 2, the system can determine the thickness of both $L_3$ and $L_4$.

Once the appropriate calculations are made, the system can then compare this data with the desired thickness data. In making this calculation, the system can speed up or slow down the pulling device 14 to more closely achieve the desired thickness of the cooled continuously manufactured product 2b. One should note that the calculations described in this disclosure are intended only to illustrate one possible example of calculating the thickness of the continuously manufactured product 21. 2b. Other calculations may also be included as part of this disclosure.

Figure 15:
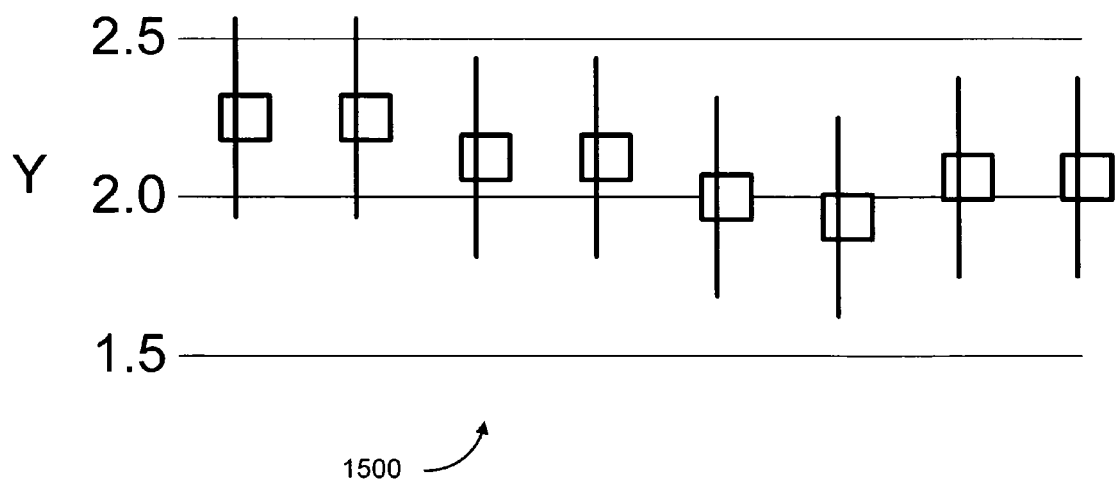
FIG. 15 is a graphical illustration of various measurements of one dimension of a shaped profile that may be taken by the material thickness system of FIG. 12.

FIG. 15 is a graphical illustration of various measurements of a dimension of a shaped profile that may be take by the material thickness system of FIG. 12. As the continuously manufactured product 2a, 2b is advancing, the die centering system 40 and the material thickness system 70 are taking measurements and making calculations. FIG. 15 illustrates a graphical representation 1500 of such information with respect to the length of the short side of a 2×4 shaped profile, with a target of 2.0 being desired. As the value increases above 2.0 the thickness of continuously manufactured product 2a, 2b is above the desired mark and the system (or operator) can adjust the pulling device 14 to reduce the thickness of the continuously manufactured product 2a, 2b. Alternatively, when the length data falls below 2.0, the system (or operator) can adjust the pulling device 14 to increase the thickness of continuously manufactured product 2a, 2b.

Figure 16:
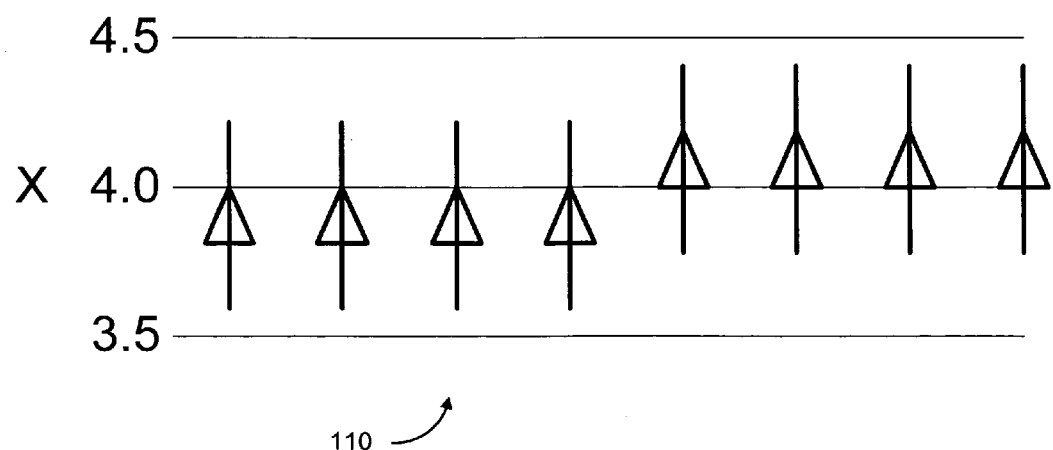
FIG. 16 is a graphical illustration of various measurements of another dimension of a shaped profile that may be taken by the material thickness system of FIG. 12.

FIG. 16 is a graphical illustration of various measurements of another dimension of a shaped profile that may be taken by the material thickness system of FIG. 12. The graphical representation 110 of the core side of a 2×4 shaped profile is illustrated with a target value of 4.0. Similar to the graphical representation 100 of FIG. 15, the system can adjust the pulling device 14 according to the received data.

Figure 17:
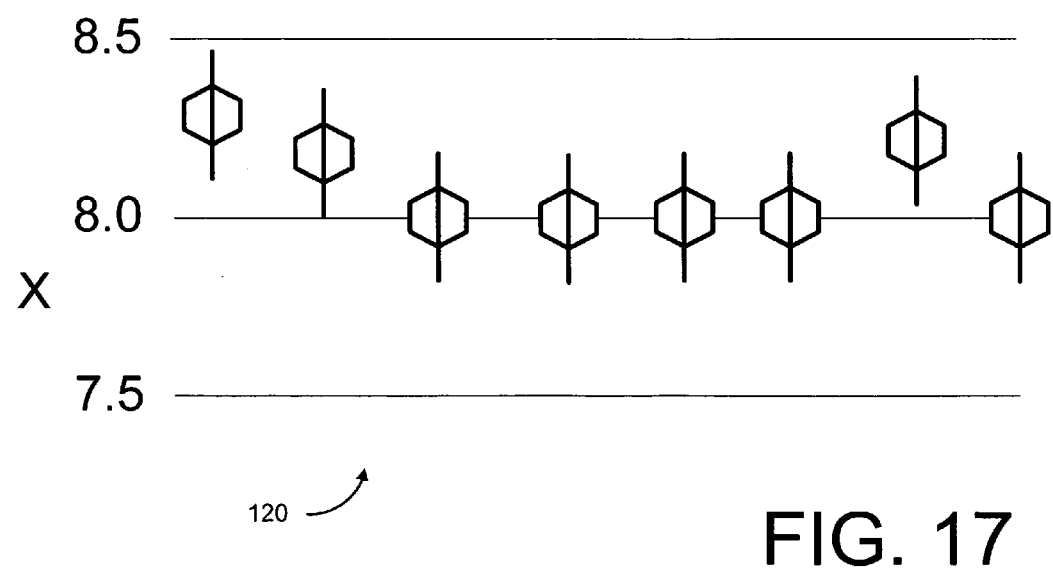
FIG. 17 is a graphical illustration of a simplified measurement of a shaped profile that may be taken by the material thickness system of FIG. 12.

FIG. 17 is a graphical illustration of a simplified measurement of a shaped profile that may be taken by the material thickness system of FIG. 12. FIG. 12 represents a graphical representation 120 of the combined data from FIGS. 16, 17. By combining the data for each side of the continuously manufactured product 2a, 2b, the system (or a user) can more easily determine how to adjust the pulling device 19 to achieve the desired results. While a graphical representation 100 from FIG. 15 is multiplied with the graphical representation 110 from FIG. 16 to achieve the graphical representation 120, this is but a nonlimiting example.

Figure 18:
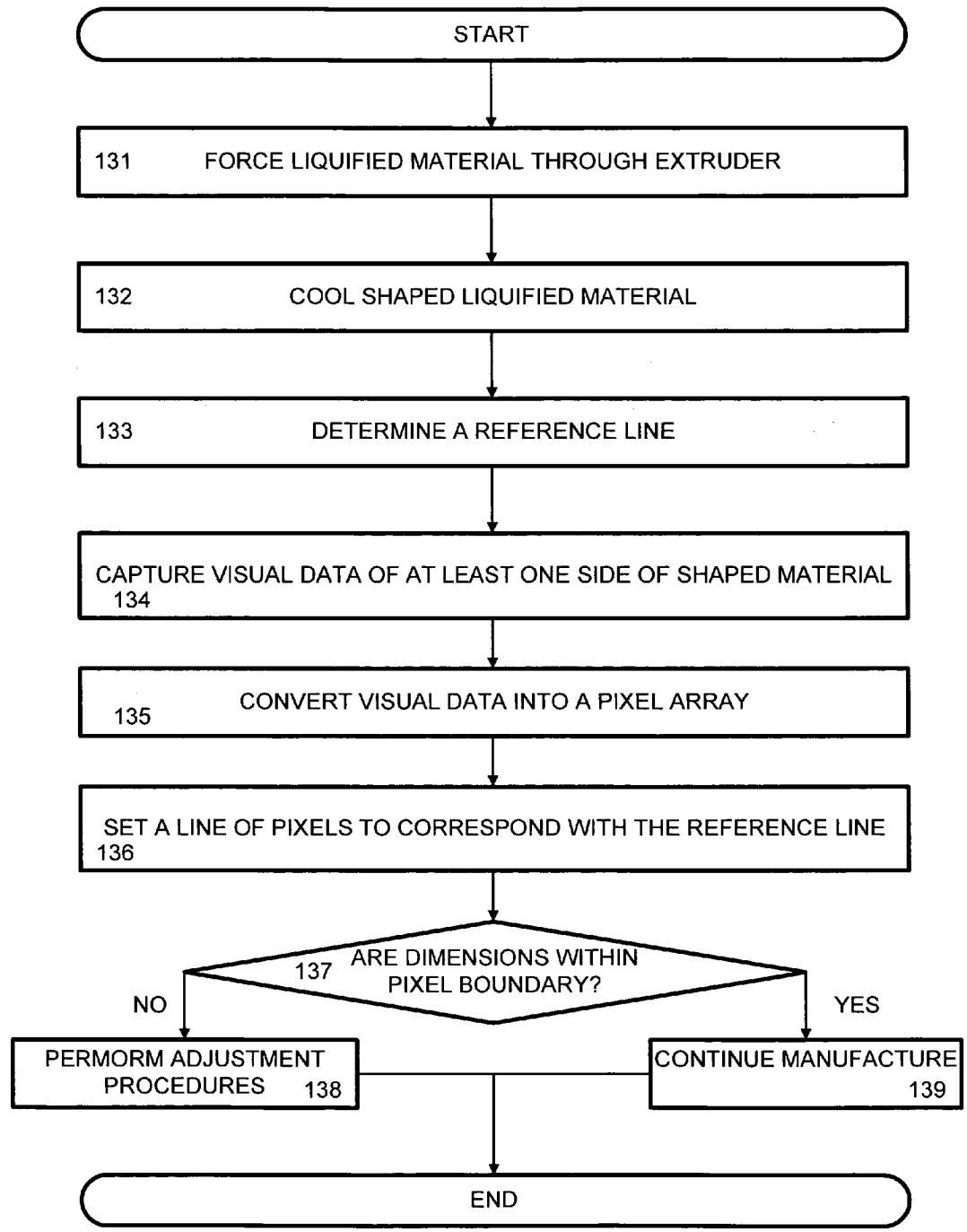
FIG. 18 is a flow chart illustrating one embodiment of possible steps that may be taken in the die setting system of FIG. 9.

FIG. 18 is a flow chart illustrating one embodiment of possible steps that may be taken in the die setting system of FIG. 9. The first step of the flowchart of FIG. 9 is forcing the liquefied material through the extruder (step 131). As discussed above, the continuously manufactured product 2a, 2b may be in the form of a liquid or amorphous solid. When the continuously manufactured product 2a, 2b is forced through the extruder 10, which includes a mandrel 24 and a die 22, which define the shaped aperture 4, the continuously manufactured product is formed to a desired shape. The next step is to cool the shaped liquefied material (step 132). This may be accomplished using the cooling device from FIGS. 6, 9, and 12, or other similar cooling means. The next step is to determine a reference line (step 133). As discussed above, the reference line helps the system determine both the position of the die 22, and the thickness of the continuously manufactured product 2a, 2b. While this step is disclosed after cooling the continuously manufactured product 2a, 2b, there is not such limitation intended. In actuality, many embodiments will have determined a reference line before manufacturing begins.

The next step is to capture visual data of at least one side of the shaped material (step 134). This can be accomplished with visual capture devices 52 or other similar means. After the visual data is captured, the system can convert the visual data into a pixel array (step 135) and set a line of pixels to correspond with the reference line (step 136). As with determining a reference line (step 133), in many embodiments, the coordination of the line of pixels with the reference line can be completed before production begins. As such, the placement of this step is not indicative of the only configuration.

The next step of this flowchart is to determine whether the dimensions are within the predefined pixel boundary (step 137). If the dimensions of the continuously manufactured product 2a, 2b are not within the acceptable range, the system may perform adjustment procedures (step 138). If, on the other hand, the dimensions are acceptable, the system can continue manufacture (step 138).

Figure 19:
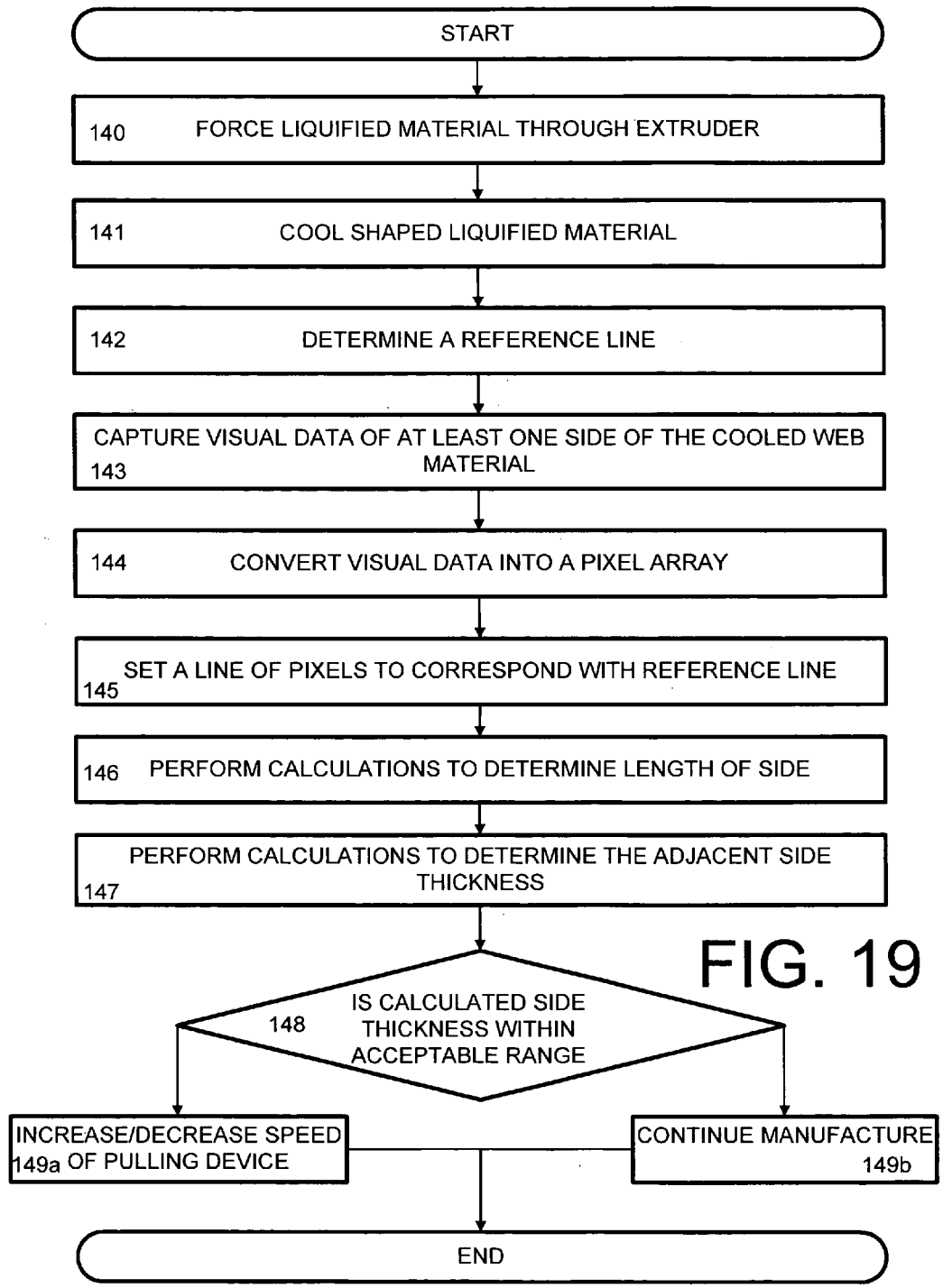
FIG. 19 is a flow chart illustrating one embodiment of possible steps that may be taken in the material thickness system of FIG. 12.

FIG. 19 is a flow chart illustrating one embodiment of possible steps that may be taken in the material thickness system of FIG. 12. Similar to the first step in the flowchart of FIG. 13, the first step in the flowchart of FIG. 19 is to force the liquefied material through the extruder (step 140). As stated above, this shapes the uncooled continuously manufactured product 2a into a desired shape. Once the uncooled continuously manufactured product 2a is shaped, it can be cooled (step 141). Cooling the uncooled continuously manufactured product 2a creates a more rigid structure by which a pulling device 14 (see FIGS. 6, 9, 12) can advance the entire web of material. The next step in the flowchart of FIG. 19 is to determine a reference line (step 142). After determining a reference line, the next step is to capture visual data of at least one side of the cooled continuously manufactured product 2b (step 143). Once the visual data is captured, the system can convert the visual data into a pixel array (step 144), and set a line of pixels to correspond with the reference line (step 145).

Next, the system can perform calculations to determine the length of the measured side of the cooled continuously manufactured product 2b (step 146) by comparing the pixel array data with the reference line. From this data, the system can perform calculations to determine the thickness of an adjacent side (step 147). From this information the system can determine whether the side thickness is within an acceptable range (step 148). If so, the system can continue manufacturing (step 149b); if not, the system can increase or decrease the speed of the pulling device 14 (step 149a).

Defect Location

Figure 20:
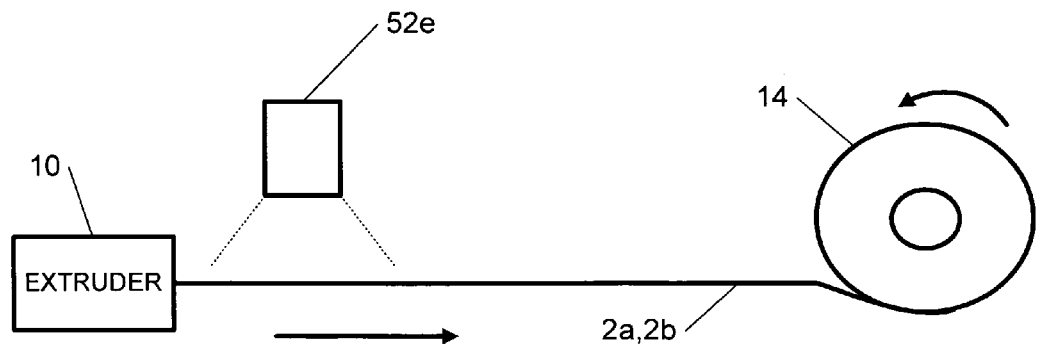
FIG. 20 is a functional block diagram of a sheet manufacturing system, similar to the system of manufacturing shaped profiles of FIG. 6.

FIG. 20 is a functional block diagram of a sheet manufacturing system, similar to the system of manufacturing shaped profiles of FIG. 6. In this embodiment, the extruder 10 may or may not be configured to shape the continuously manufactured product 2a, 2b into a shaped profile. Regardless, visual data capture device 52e is configured to detect defects associated with the continuously manufactured product 2a, 2b using methods similar to those discussed above. Pulling device 14 advances the continuously manufactured product 2a, 2b in the direction of the arrow.

Figure 21:
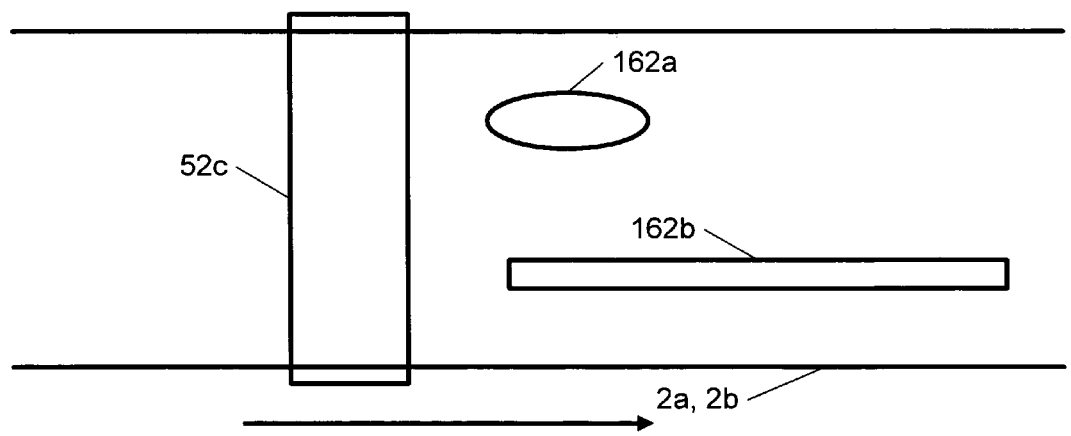
FIG. 21 is an overhead view of the sheet manufacturing system of FIG. 20.

FIG. 21 is an overhead view of the sheet manufacturing system of FIG. 20. As shown, defects 162a, 162b on the continuously manufactured product 2a, 2b pass by the visual capture device 52e. The visual capture device in this embodiment is configured to detect and locate defects, which may include any of the following: streaks, spots, holes, formation defects, pattern defects, and opacity defects. The visual data received by the visual data capture device 52e can then be converted into a pixel array, and associated with a reference line.

Figure 22:
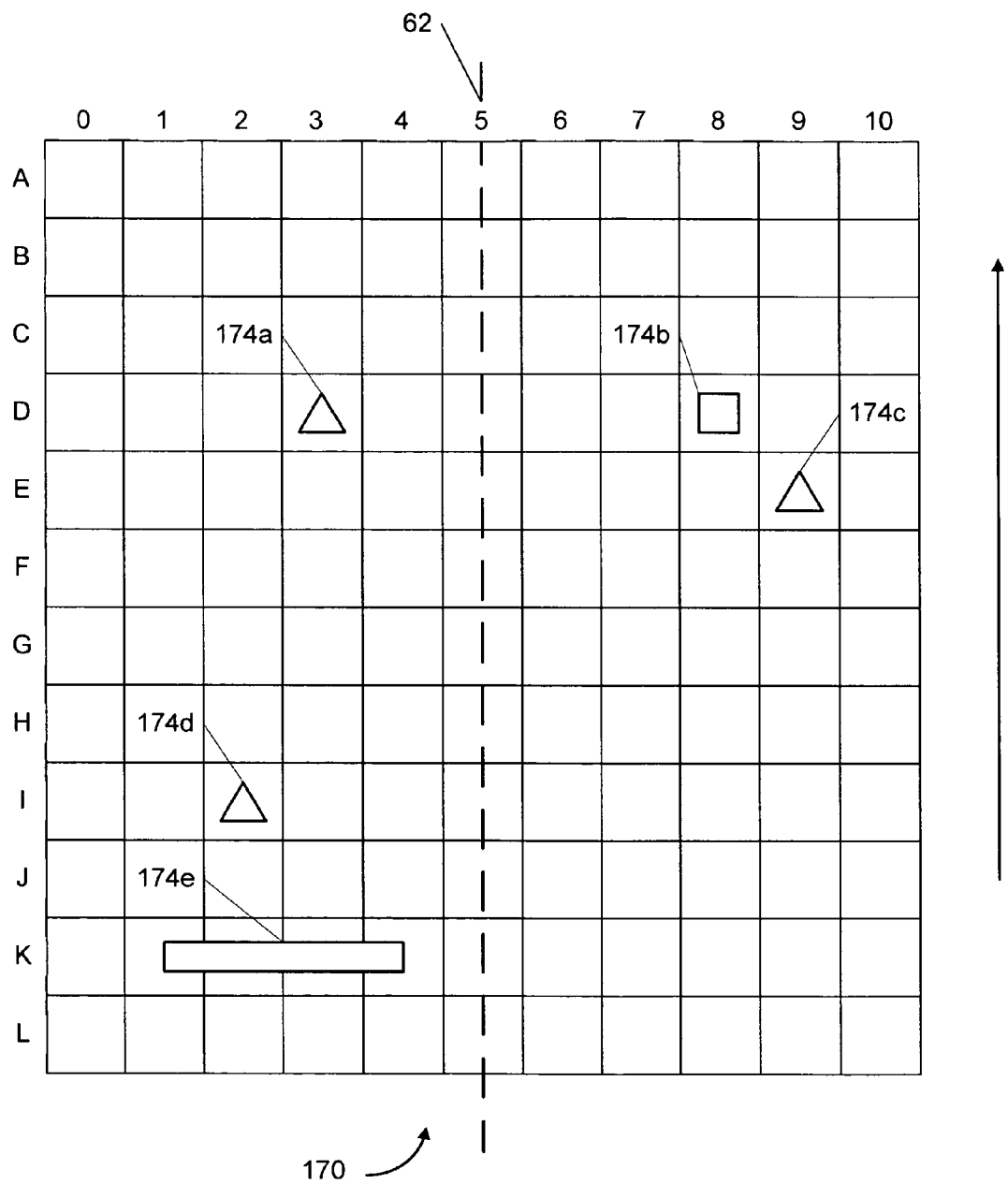
FIG. 22 is a functional block diagram of a pixel array with defects, generated by the sheet manufacturing system of FIGS. 20 and 21.

FIG. 22 is a functional block diagram of a pixel array with defects, generated by the sheet manufacturing system of FIGS. 20 and 21. The pixel array of FIG. 22 illustrates that each defect 174a, 174b, 174c, 174d, and 174e can be charted according to the pixel array and reference line 62. In this embodiment the continuously manufactured product 2a, 2b is advancing in the direction of the arrow, with the reference line 62 being parallel to the direction of advancement. In at least one embodiment the visual capture device 52e (from FIGS. 20 and 21) records the visual data as a series of "snapshots" that are analyzed individually for defects. In this scenario, each snapshot labeled, along with the location of the defect on that snapshot. Alternatively, the visual data capture device 52e can be configured to capture visual data such that a single pixel array is created for a continuously manufactured product.

Figure 23:
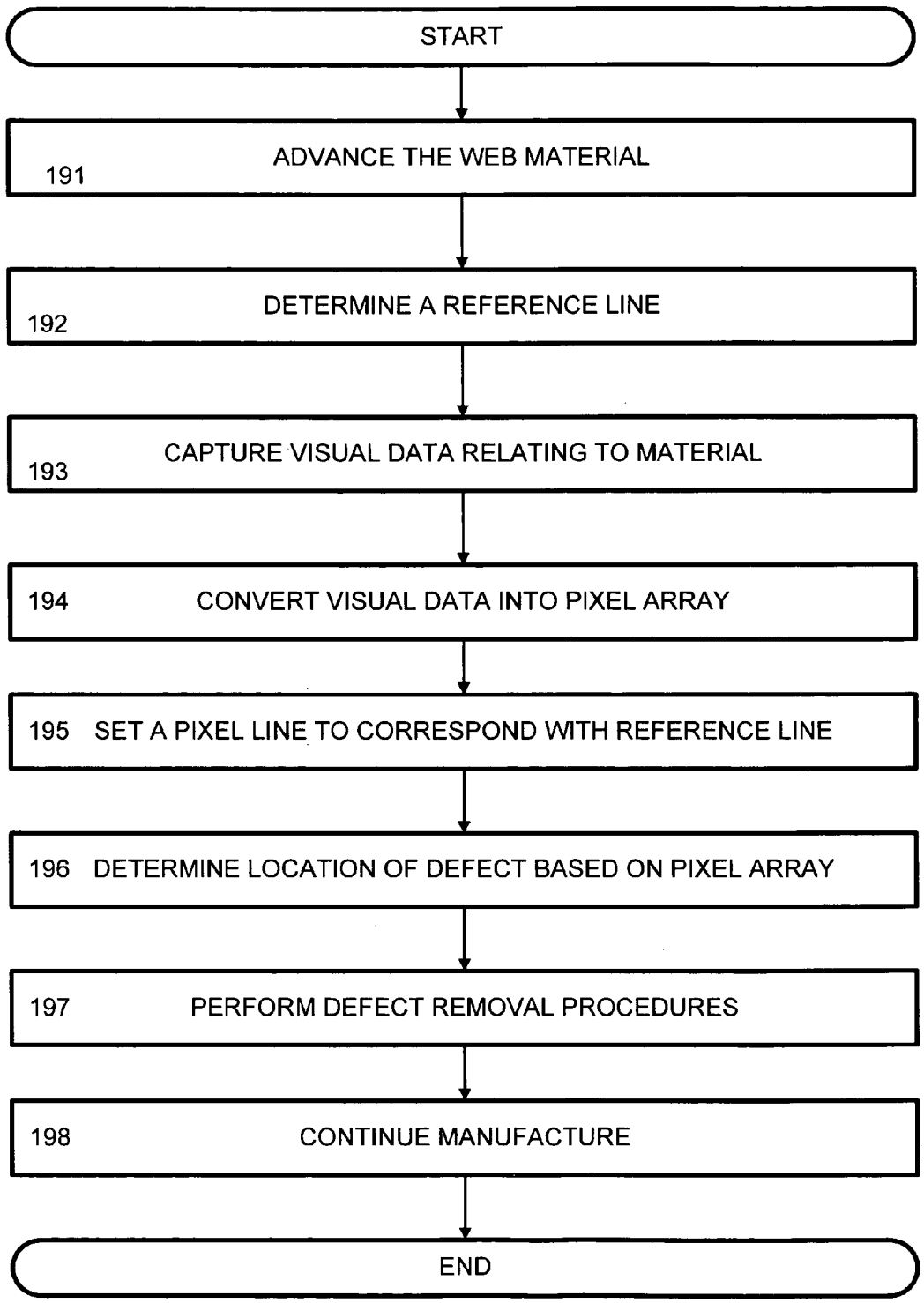
FIG. 23 is a flowchart of possible steps that may be taken to detect defects in the system of FIG. 20.

FIG. 23 is a flowchart of possible steps that may be taken to detect defects in the system of FIG. 20. The first step in this flowchart is to advance the continuously manufactured product (step 191). Then the system determines a reference line (step 192). Next, the system captures visual data relating to the continuously manufactured product (step 193), and converts the visual data into a pixel array (step 194). Then, the system can set a pixel line to correspond with the reference line (step 195). The system can then determine the location of the defect based on the pixel array (step 196). With this data, removal procedures can be performed (step 197) and manufacture can continue (198).

Width and Length Measurement

FIG. 24A is a screenshot of a typical work product, as illustrated in FIG. 2. Assuming the lighting is wider than the web, the system could very easily detect the edge of the material and because of the pixel positions across the whole field of view of the camera, it is also very easy to tell the difference between the materials edges shrinking or growing and the web centerline wandering which gives an apparent edge shift. As illustrated, FIG. 24A includes a work product 2 that can be continuously manufactured. The work product has a predetermined width 2464 and a continuous length. While the width 2464 is generally designed to remain constant through the manufacturing process (unless cut for a particular use), the length can be any length. However, for any given screenshot, the length will typically have a finite length 2466, and the predetermined width 2464.

FIG. 24B is a screenshot of a typical line camera scan of the work product from FIG. 24B. As illustrated the line camera scan includes an x-axis 2452 and a y-axis 2454. The x-axis 2452 in this nonlimiting example relates to the number of pixels in a typical width sensor, and the y-axis 2454 can be any value, depending on other measurements of the work product. Additionally, FIG. 24B illustrates a work product presence signal 2456 that illustrates the presence of the work product between width reference lines 2462a, 2462b. Outside of width reference lines 2462a, 2462b are work product absence signals 2458a, 2458b. As is evident, the lack of continuity between the work product presence signal 2456 and the work product absence signals 2458a, 2458b. In FIG. 24B, the work product resides at approximately x=1700 pixels and x=3200 pixels. The width reference lines 2462a, 2462b may be generated and placed on an operator station to indicate the desired width position of the work product. An operator (or the system itself) may adjust the manufacturing process if the work product presence signal 2456 extends beyond the width reference lines 2462a, 2462b or if the work product absence signals 2458a, 2458b extend beyond the width reference lines 2462a, 2462b.

Figure 25:
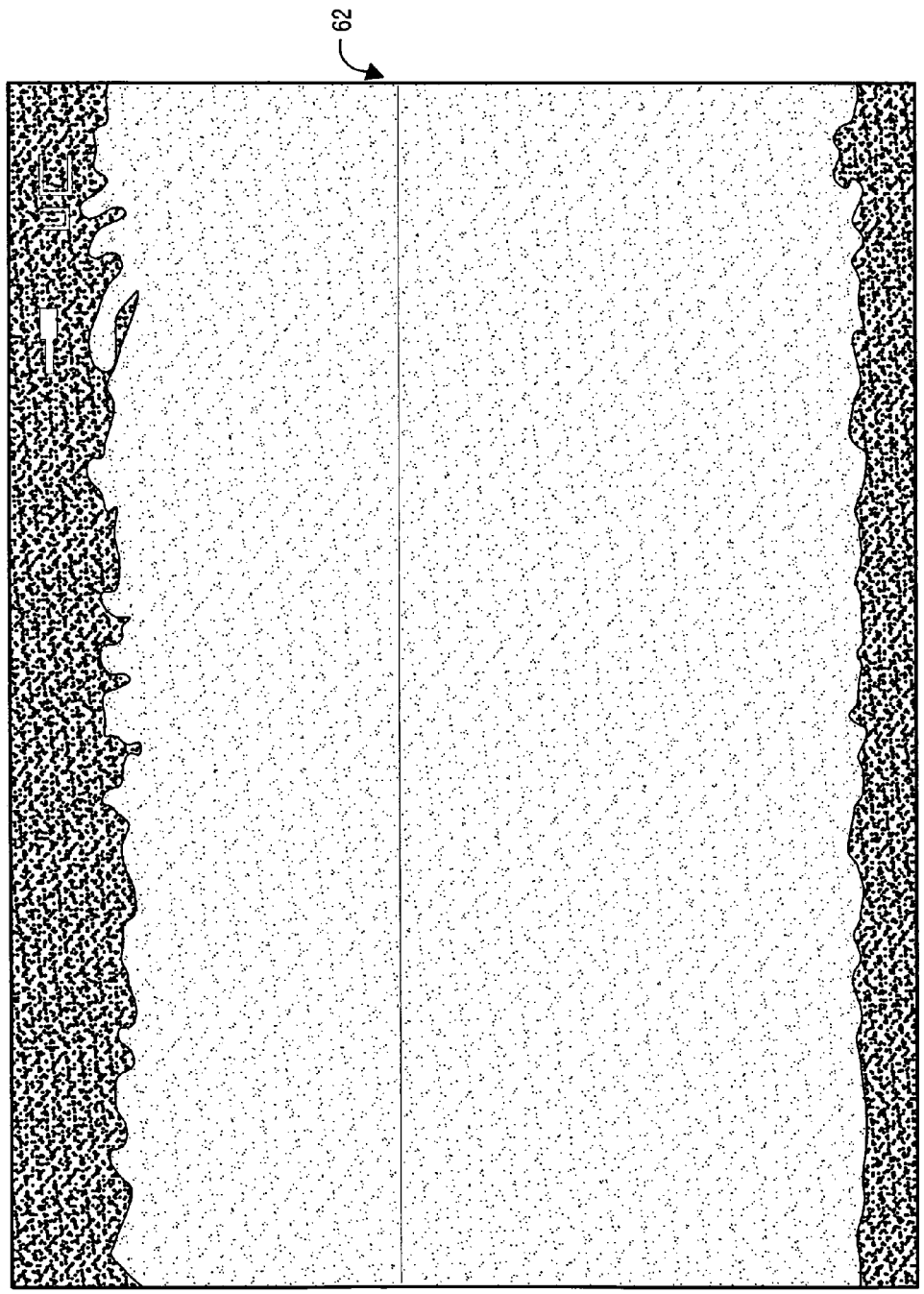
FIG. 25 is an exemplary diagram of a work product and a reference line as described with reference to FIGS. 24A and 24B, which can be used to determine width and control slitters.

FIG. 25 is an exemplary diagram of a work product and a reference line as described with reference to FIGS. 24A and 24B. As illustrated, a desired cutting reference line 2562 is shown on a piece of tufted carpet. This line is measured and controlled by pixel positions. While the width reference lines 2462a, 2462b from FIG. 24B illustrated the width boundary of a work product, the desired cutting reference line 2562 indicates a desired position for cutting the work product. In at least one embodiment, width reference lines and sensors can measure the accuracy of the cut defined by desired cutting reference line 2562 at various other points in the manufacturing process.

This same technique can be used for the other dimension, length as well. Some materials are used to make parts such as vinyl siding and lighting lenses. Because the data is accumulated so rapidly it is relatively easy to gather data on the length dimension as well. The camera system sketched in FIG. 2 could measure the length of any given part to less than ⅒ of an inch for any line running at speeds of 60 feet per minute (FPM) or less.

Figure 26:
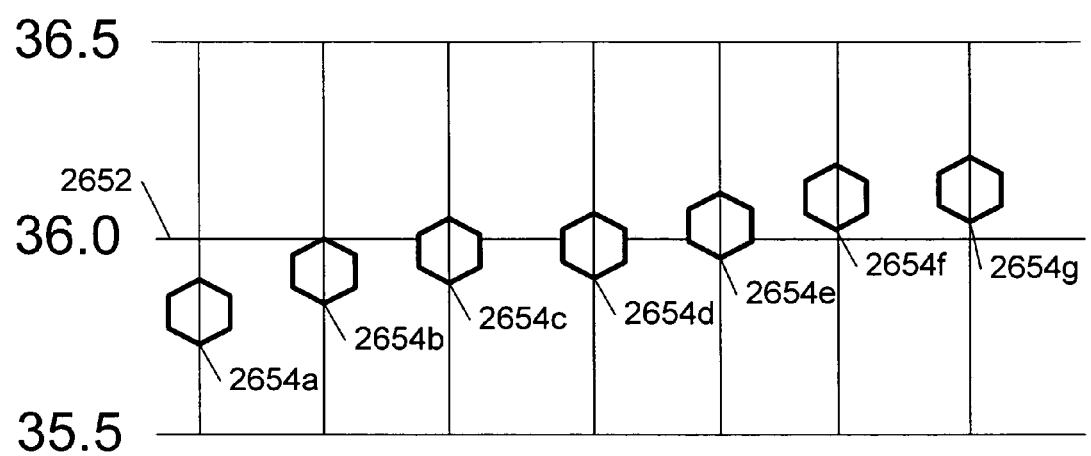
FIG. 26 is simulated trend graph of a length measurement on a part shearing operation, similar to the trend graph from FIG. 15.

FIG. 26 is simulated trend graph of a length measurement on a part shearing operation, similar to the trend graph from FIG. 15. As illustrated, this graph includes a desired length 2652, which has a value of 36.0. The measurement points 2654a-2654g illustrate the particular measurement taken, and indicate a trend of the work product over a predetermined distance. In this particular nonlimiting example, the trend for the work product length is increasing beyond the desired length of 36.0. Therefore, material costs are increasing and work product quality is decreasing. By supplying this data to an operator or system computer, adjustments can be made perhaps in real time and save both time and money.

Coating Measurement

For various reasons a coating material may be applied to a work product during manufacture. Depending on the particular work product, the particular coating applied, and the desired use of the final product, a predetermined coating thickness or coating weight is generally desired. As discussed above, variance from the predetermined desired measurements can reduce quality and increase raw material costs.

Figure 27A:
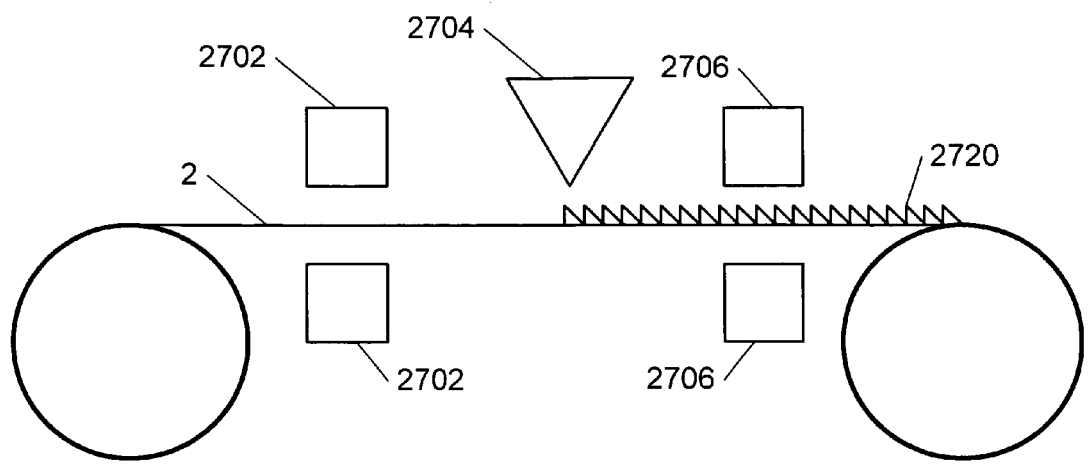
FIG. 27A is a functional block diagram of a coating technique for a work product that employs of both nuclear gauging and Infrared (IR) gauging, similar to the system from FIG. 2.

FIG. 27A is a functional block diagram of a coating technique for a work product that employs of both nuclear gauging and Infrared (IR) gauging. The uncoated work product 2 is measured by the first gauge 2702, which is called the base gauge. The device 2704 applies the coating and the coated material is measured again by the gauge device 2706, which is called the total gauge. The base signal from the base gauge 2702 is subtracted from the total signal generated by total gauge 2706 and the net result is the weight or thickness of the coating applied.

Figure 27B:
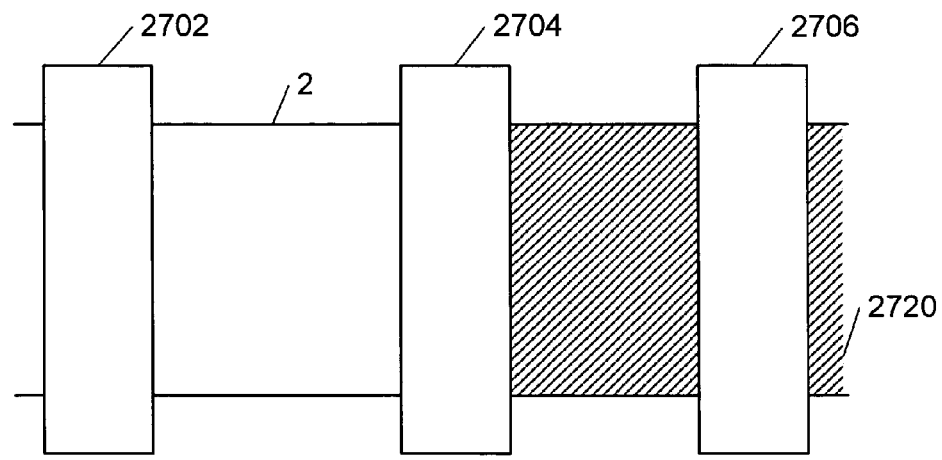
FIG. 27B is an exemplary depiction of the coating technique from FIG. 27A.

FIG. 27B is an exemplary depiction of the coating technique from FIG. 27A. As illustrated from this top view, the coating 2720 is applied to the work product 2 by device 2704. The measurement from the base gauge 2702 is subtracted from the measurement from total gauge 2706 and the net result includes the weight or thickness of the coating applied.

Figure 27C:
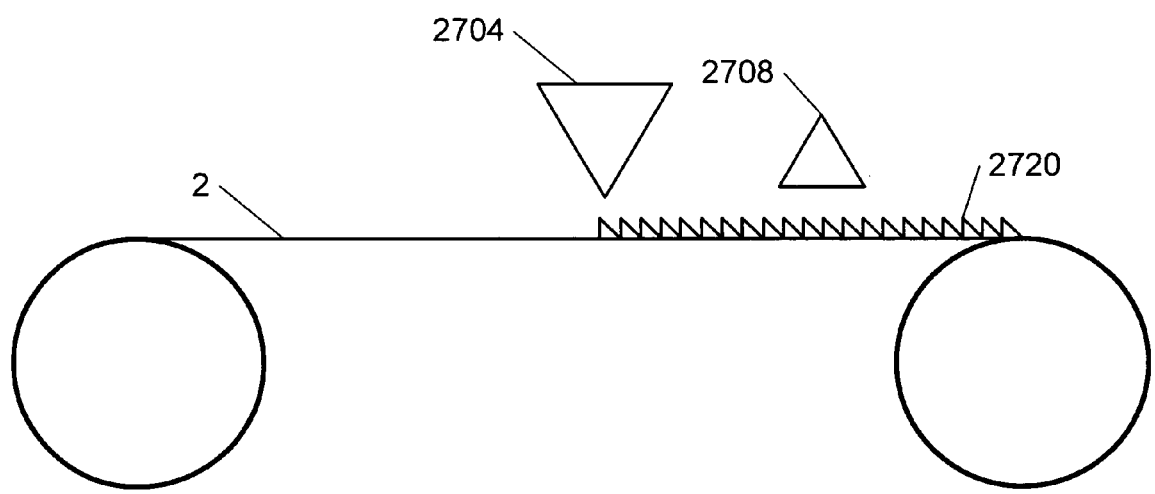
FIG. 27C is an additional exemplary depiction of the coating technique from FIG. 27A.

FIG. 27C is an additional exemplary depiction of the coating technique from FIG. 27A. In this case the IR gauge is looking at the coating with two different near infrared wavelengths. By comparing these two signals the gauge can measure the coat weight directly without having to measure the base material as shown in the above example using nuclear gauging.

FIG. 28A is a screen shot diagram of out put data from either gauging system scanning the width of a moving work product that can be taken from FIGS. 27A, 27B, 27C. As illustrated, the coating measurements approach a desired value at approximately x=8.8(2804) and x=32(2804*b*). Between these values the coating measurement reaches an error of approximately 4%. While the discussed techniques can perform various coating measurements, the present disclosure also includes a similar measurement technique to develop the same data described in FIG. 28A without the using a scanner that traverses the width of the work product.

FIG. 28B is a sketch of an infrared spectrograph related to the measurement techniques illustrated in FIG. 27C. The x-axis represents the wavelength of light. In general, this is plotted over a range in the infrared frequency region (i.e. above the visible light spectrum, which can include a range of 0.8 microns to as high as 15 microns). The y-axis represents a percent transmission. When light impinges on a piece of material the light will typically be reflected, scattered, absorbed and transmitted. The y-axis in FIG. 28B provides a value for the scattered, absorbed and transmitted portions of the four events. In general terms the reflected portion is small, typically less than 4% of the original beam and is generally constant except when the incident material approaches 12 microns in thickness. For the purpose of this discussion the reflected light will always be considered constant.

Absorption is directly related to the mass of the material being investigated. If one can measure the amount of absorbed light at certain wavelengths this data can be used to make an absolute measurement of the material being produced in real time. From FIG. 28B, when $\lambda_1$ 2820 is compared to $\lambda_2$ 2822 the real difference in percent transmission is due to absorption and thus a continuous measurement can be made by comparing these signals and the proper calculation made in the software.

Figure 29:
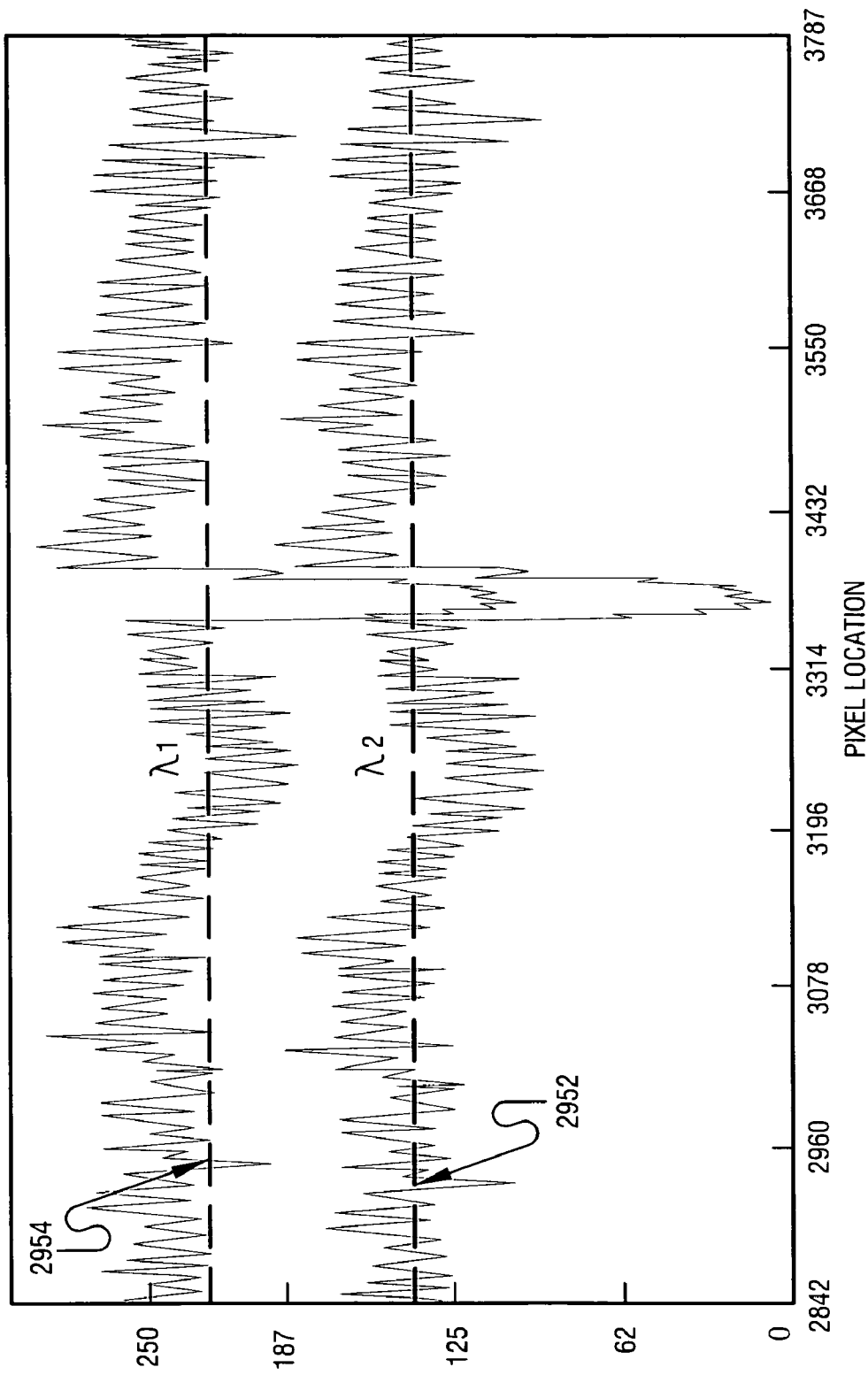
FIG. 29 is a screenshot of a coating measurement taken pursuant to a coating system, similar to the system from FIGS. 27A, 27B, and 27C.

FIG. 29 is a screen shot of a coating measurement taken pursuant to a coating system, similar to the system from FIG. 27C. As illustrated this data represents data captured by two cameras taking line scans of reflected light. If these two cameras have an appropriate narrow band pass filter over each lens, it is possible to generate two distinct signals 2952, 2954. These two signals can relate to the absorption characteristics of the coating materials as determined by real IR spectroscopy and sketched in FIG. 28B. The first signal wavelength 2952 can be a reference wavelength and the other signal wavelength 2954 can represent an appropriate absorption wavelength. From these two signals an appropriate measurement can be made to the coating weight to develop the software graphics illustrated in FIG. 28A.

By taking advantage of these techniques, various benefits can be realized. First since the field of view of the plurality of cameras can cover the entire web surface, the measurement can cover the entire web continuously. The camera capabilities and web size may generally determine the number of cameras desired. Second, because the camera (or cameras) is fixed, each signal can be taken from the same point in the production direction flow, thus eliminating any variation affects to the measurement from the product. Thirdly, because full web coverage with the cameras is achieved, the system does not require a scanner. With fewer moving parts there are typically fewer maintenance issues. Fourth, the system can be configured to provide three-dimensional graphics real time, without the requirement to use radiation. Fifth, pixel and gray scale values can be grouped properly to provide the system with the proper information to automatically control the coating whether it was put on by a roll coater or a slot die. In addition, it is entirely possible that that the control scheme will be improved because the software does not have to wait until an individual sensor traverses the web for determining the coating weight across the entire sheet and thus the response time of the control would be improved.

Film Thickness Measurement

Figure 30:
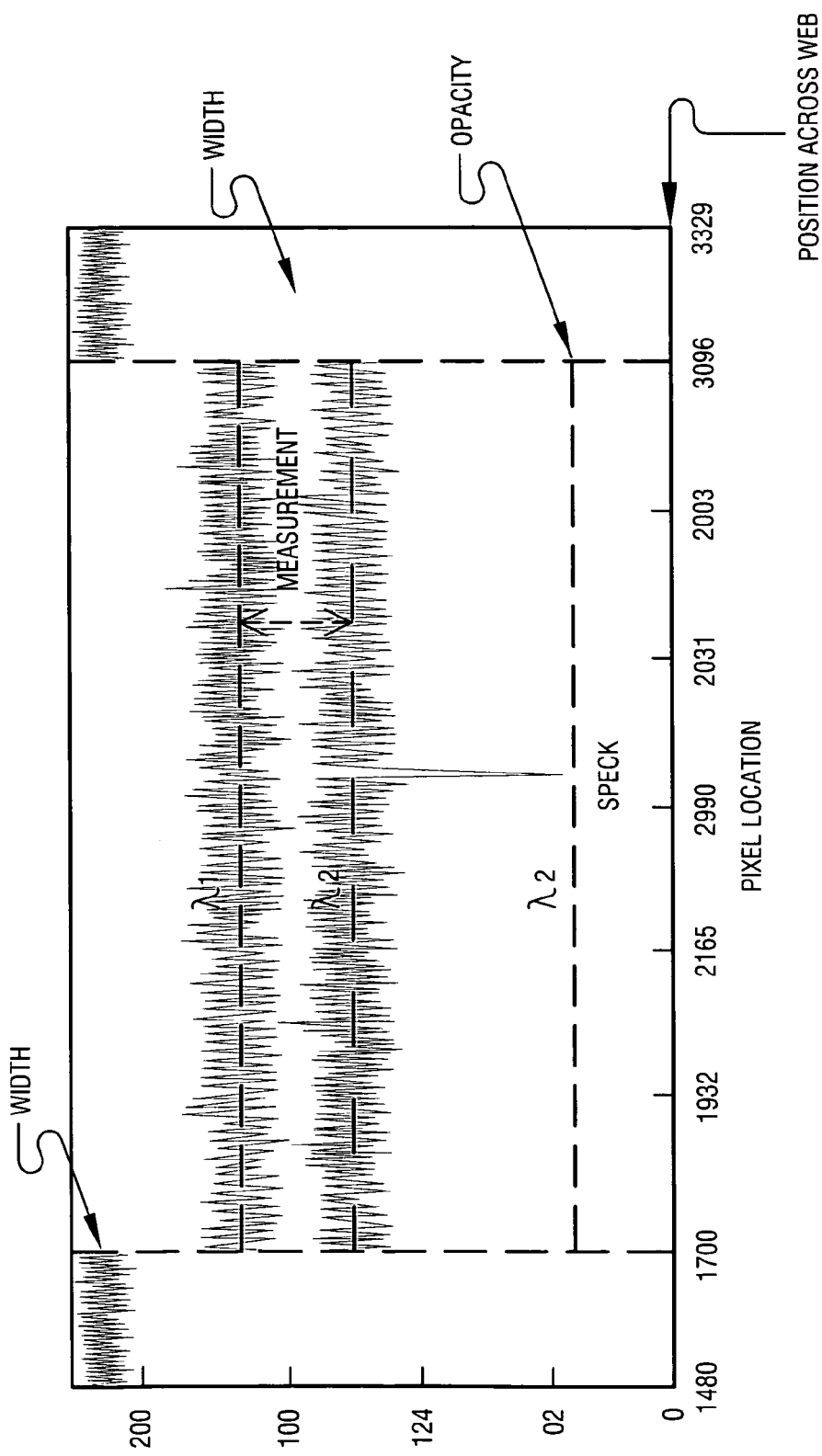
FIG. 30 is a screenshot of a film thickness measurement, similar to the screenshots from FIGS. 24 and 29.

FIG. 30 is a screen shot of a film thickness measurement as the film is being extruded, similar to the screen shot in FIG. 29 where a coating measurement is being made. In this nonlimiting example, light can be transmitted through the film and the cameras can be directed toward the light from a position over the sheet similar to the configuration illustrated in FIG. 2. As in the case of the coating measurement, two different wavelengths can measure the thickness of the polymer being extruded. In addition, one or more of these same cameras could look at the overall width of the material and distinguish between web wander and actual width changes. Simultaneously one or more of the cameras can configured to search for defects such as carbon spots and also measure changes in light transmissivity that are related to the opacity of the film.

It is also conceivable that this measurement data can be used in the automatic control of the process in lieu of a traditional scanning sensor. As a nonlimiting example, by grouping the gray scale data by pixel position to the number of die bolts on the extruder die, the data can be used to adjust the die and make a more uniform product. Similarly the average of all the gray scale data can be compared to the sheet average and used as a reference point for auto control. Some of the main advantages of the camera pixel system are the removal or reduction of radiation, no scanning sensor, virtually no moving parts, and potentially faster automatic control times. Perhaps the most attractive feature of all, is that all of the camera measurement techniques can be made with existing hardware and new developments are not required.

Opacity

Opacity is a measure of the inverse of light transmission through a material. If a material is completely transparent, it can be assigned a grayscale value of 256 to a camera system. Alternatively, if the material is completely opaque it can be assigned a grayscale value of zero. Grayscale values between 0 and 256 are reserved for varying opacity of materials.

In at least one nonlimiting example, a piece of film from a trash bag can be made to appear opaque, thereby hiding the contents within. However, if the film is laid directly on a printed page the print is easily read through the trash bag. Because the trash bag needs only to be partially opaque, measurement and control of this component is desired.

Tappi has a procedure to determine the opacity level of a given film for optimum printing conditions. As a nonlimiting example, one can assume a desired opacity value of 60% opaque, which is opaque enough to appear completely opaque from most distances. If the actual material opacity is 65% opaque or 75% opaque, a casual observer will typically be unable to notice any difference, as all three materials will likely look the same. Thus, it is advantageous to measure opacity in absolute units to insure that the correct amount of additives is being used because the use of more additives is not detectable and does not enhance the visual performance of the material.

Figure 31:
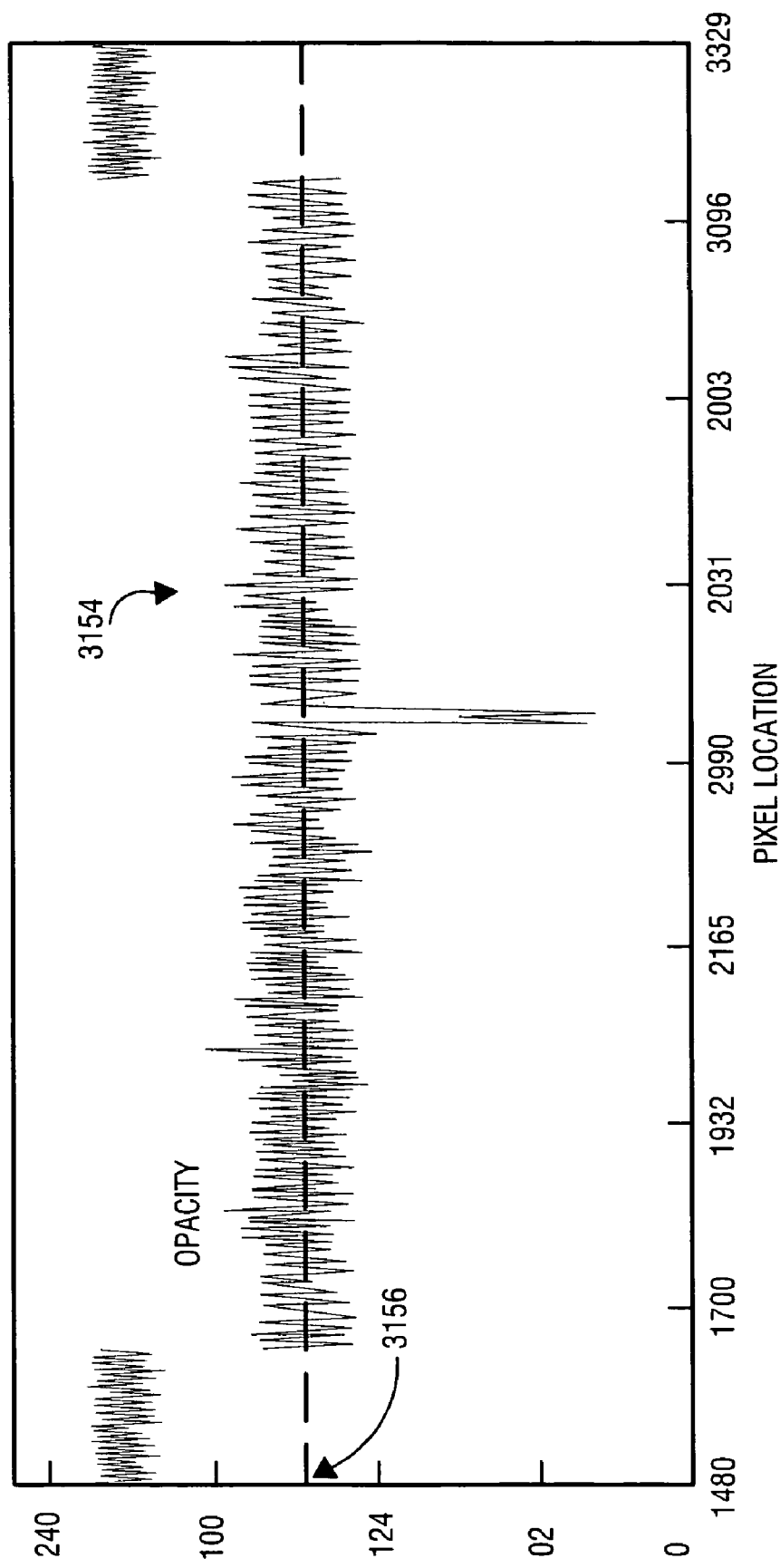
FIG. 31 is a screenshot data received from an opacity sensor coupled to the pixel positioning system, as illustrated in FIGS. 24, 29, and 30.

FIG. 31 is a screenshot data received from an opacity sensor coupled to the pixel positioning system, as illustrated in FIGS. 24, 29, and 30. As discussed above, the work product may include various components to measure and control. As illustrated an opacity signal 3154 can be measured and compared with a desired opacity reference line 3156. If the grayscale value decreases, the material is becoming more opaque. Conversely, if the grayscale value increases, the work product is becoming more translucent. One reason for making an on-line measurement is to reduce the use of raw materials as additives and to certify that the proper opacity values are being met. By continuously measuring the opacity while the work product is being produced, adjustments can be made more quickly to provide a higher quality product, and reduce costs in the use of raw materials.

One should also note that while certain measurements are explicitly described in this disclosure, other measurements can also be made, pursuant to the techniques disclosed herein. As a nonlimiting example, other measurements such as moisture content, temperature, and other measurements are also included in the scope of this disclosure.

It should be emphasized that many variations and modifications may be made to the above-described embodiments. All such modifications and variations are intended to be included herein within the scope of this disclosure and protected by the following claims.

The invention claimed is:

1. A continuous manufacturing process, comprising:
advancing, by a machine, a work product in a direction along a processing path;
directing a light signal on one side of the processing path to establish silhouette data;
capturing silhouette data related to the work product;
converting the silhouette data into a pixel array;
setting a predetermined line of pixels in the sensor array as a reference line that runs along the desired processing path and overlays the path traveled by the work product; and
counting a number of pixels in the pixel array in a plurality of directions perpendicular from the reference line; and
determining based on the count whether the work product has twisted with regard to a predetermined desired position.

2. The process of claim 1, further comprising determining the position of a terminal boundary of the work product based on data from the pixel array.

3. The process of claim 1, further comprising using the pixel array to determine whether the work product is out of position with respect to the reference line.

4. The process of claim 1, further comprising using the pixel array to locate at least one defect in the work product.

5. The process of claim 4, wherein the defect includes at least one of the following: a pattern error, a formation error, an opacity defect, and a coating defect.

6. The process of claim 1, further comprising using the pixel array to determine thickness data of at least one side of the work product.

7. The process of claim 6, further comprising adjusting the speed of advancing the work product in response to a change in the thickness data.

8. The process of claim 7, further comprising calculating a target number from the thickness data, the target number configured to assist in determining a desired speed for the pulling device.

9. A pixel positioning system, comprising
a visual data capture device, the visual data capture device configured to capture visual data relating to a continuously manufactured work product moving along a processing path;
first logic configured to convert the visual data into a pixel array, wherein the pixel array is associated with a reference line overlaying the processing path, the reference line further being configured for alignment along the processing path the processing path of the continuously manufactured work product;
second logic configured to determine and locate a defect on the continuously manufactured work product based on information from the pixel array; and
third logic configured to count a number of pixels in the pixel array in a plurality of directions perpendicular from the reference line; and
determining based on the count whether the work product is twisted with regard to a predetermined desired position.

10. The pixel positioning system of claim 9, wherein the visual capture device includes at least one of the following: a camera, a line scan camera, an Infrared (IR) blocking filter, and a light source.

11. The pixel positioning system of claim 9, wherein the defect includes at least one of the following: a pattern error, a formation error, an opacity defect, a work product thickness defect, a coating defect, a defect related to the width of the work product, and a defect related to the length of the work product.

12. The process of claim 1, wherein the work product includes continuously manufactured paper.

13. The process of claim 1, further comprising:
applying a coating to the work product; and
determining a thickness of the coating.

14. The process of claim 13, wherein determining a thickness includes utilizing at least one of the following: an infrared (IR) gauge and a nuclear gauge.

15. A pixel positioning system, comprising:
a computing device for receiving visual data for a continuously manufactured work product moving along a processing path, the computing device storing logic that performs at least the following;
determine a reference line with regard to the work product, the reference line configured as a straight line directed in the direction of the processing path and overlaying the processing path;
convert the visual data into a pixel array, the pixel array being aligned such that the reference line is positioned along a midpoint of the pixel array;
receive the visual data configured as light data that shines through the work product to cast a silhouette of at least one defect in the work product;
utilize the received visual data in reference to the pixel array and the reference line to determine a location of the at least one defect on the continuously manufactured work product; and
count a number of pixels in the pixel array in a plurality of directions perpendicular from the reference line; and
determining based on the count whether the work product is twisted with regard to a predetermined desired position.

16. The pixel positioning system of claim 15, the computing device further storing logic that determines a thickness of a coating that has been applied to the work product.

* * * * *